United States Patent
Ogura et al.

(10) Patent No.: US 6,796,946 B2
(45) Date of Patent: Sep. 28, 2004

(54) ARTERIOSTENOSIS INSPECTING APPARATUS AND ANKLE-BLOOD-PRESSURE MEASURING APPARATUS

(75) Inventors: Toshihiko Ogura, Komaki (JP); Kiyoyuki Narimatsu, Komaki (JP)

(73) Assignee: Colin Medical Technology Corporation, Komaki (JP)

( * ) Notice: Subject to any disclaimer, the term of this patent is extended or adjusted under 35 U.S.C. 154(b) by 0 days.

(21) Appl. No.: 10/370,503

(22) Filed: Feb. 24, 2003

(65) Prior Publication Data

US 2003/0212334 A1 Nov. 13, 2003

(30) Foreign Application Priority Data

May 7, 2002 (JP) .......................................... 2002-131848

(51) Int. Cl.[7] .................................................. A61B 5/00
(52) U.S. Cl. ...................................... 600/500; 600/485
(58) Field of Search ................................ 600/485, 490, 600/493–6, 500–3

(56) References Cited

U.S. PATENT DOCUMENTS

| | | | |
|---|---|---|---|
| 4,437,470 A | | 3/1984 | Prost |
| 5,791,348 A | * | 8/1998 | Aung et al. .................. 600/493 |
| 6,283,922 B1 | * | 9/2001 | Goto et al. .................. 600/485 |
| 6,355,000 B1 | | 3/2002 | Ogura |
| 2002/0026120 A1 | | 2/2002 | Ogura et al. |

FOREIGN PATENT DOCUMENTS

| | | |
|---|---|---|
| EP | 0 891 740 A1 | 1/1999 |
| EP | 1 080 685 A1 | 3/2001 |
| WO | WO 02/24053 A2 | 3/2002 |

* cited by examiner

Primary Examiner—Robert L. Nasser
(74) Attorney, Agent, or Firm—Oliff & Berridge, PLC

(57) ABSTRACT

An ankle-blood-pressure measuring apparatus for measuring a blood pressure of an ankle of a living subject, including an inflatable cuff which is adapted to be worn on the ankle of the subject; a cuff-pressure changing device which decreases a pressure in the cuff from a pressure higher than a systolic blood pressure of the ankle; a distal-pulse-wave detecting device which is adapted to be worn on a distal portion of the subject that is located on a distal side of the ankle and detects a distal pulse wave produced from the distal portion; an increasing-point detecting device for detecting at least one increasing point where a magnitude of the distal pulse wave continuously detected by the distal-pulse-wave detecting device when the pressure of the cuff is decreased by the cuff-pressure changing device, significantly increases; and an ankle-blood-pressure determining device which determines a pressure of the cuff when the increasing-point detecting device detects the second increasing point, as a systolic blood pressure of one of a plurality of tibial arteries of the ankle of the subject that has stenosis.

4 Claims, 14 Drawing Sheets

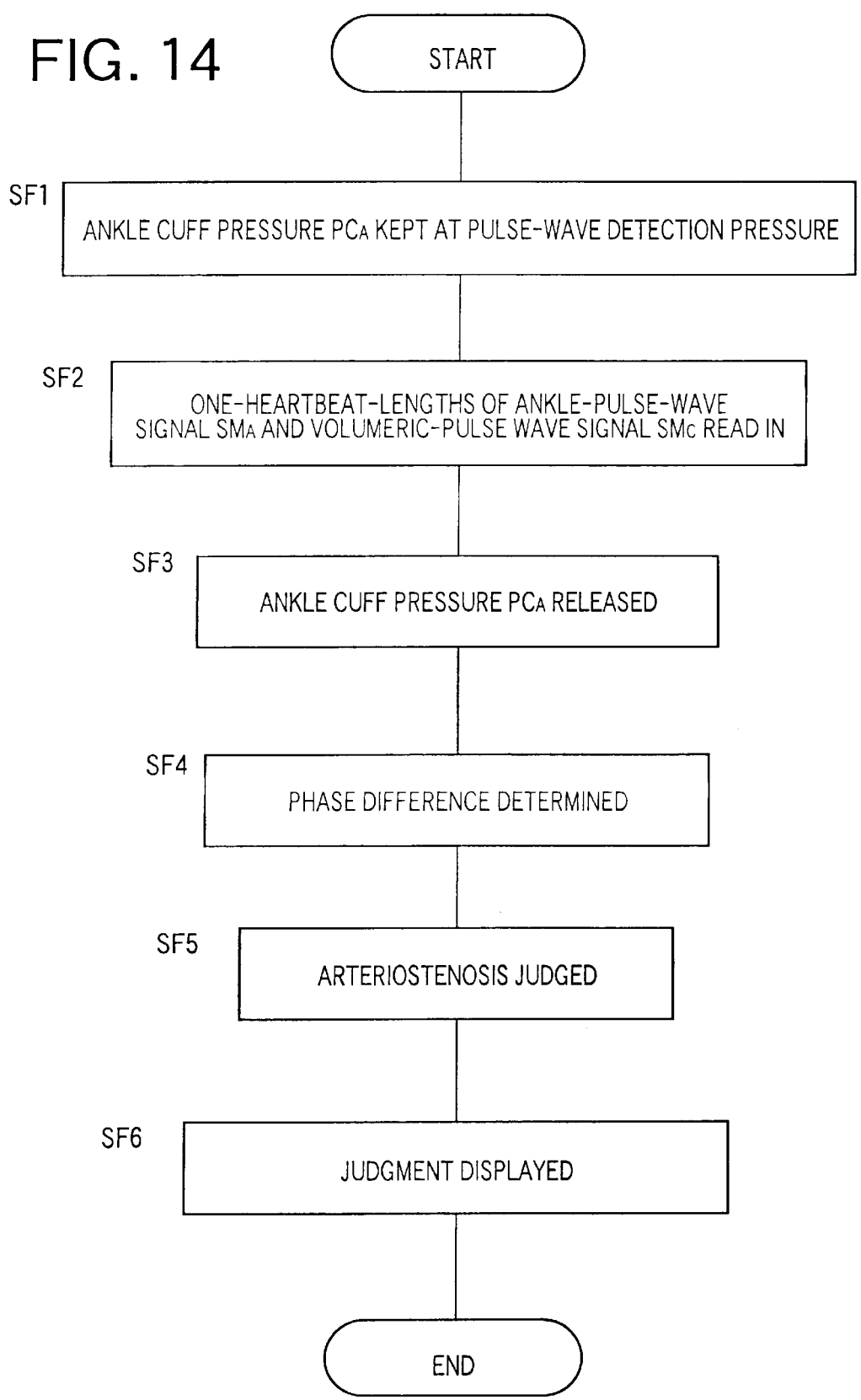

ARTERIOSTENOSIS INSPECTING APPARATUS AND ANKLE-BLOOD-PRESSURE MEASURING APPARATUS

BACKGROUND OF THE INVENTION

1. Field of the Invention

The present invention relates to an arteriostenosis inspecting apparatus which inspects presence or absence of arteriostenosis of a living person, and an ankle-blood-pressure measuring apparatus which measures a blood-pressure of an ankle of a living subject.

2. Related Art Statement

Atherosclerosis as a sort of arteriosclerosis is a disease that lipid, in particular, cholesterol deposits on walls of arteries and thereby thickens the arterial walls. Since atherosclerosis generates stenosis of an artery and thereby decreases its diameter, it is also called arteriostenosis or arteriosclerosis obliterans. There is known an inferior-and-superior-limb-blood-pressure-index measuring apparatus which can be used for inspecting arteriostenosis, by utilizing a fact that blood pressure lowers on a distal side of a body portion having arteriostenosis. The measuring apparatus is disclosed in, e.g., Japanese Patent No. 3,140,007 or its corresponding U.S. Pat. No. 6,355,000. The disclosed measuring apparatus includes a cuff worn on an inferior limb to measure a blood pressure of the inferior limb, and a cuff worn on a superior limb to measure a blood pressure of the superior limb, calculates an inferior-and-superior-limb blood-pressure index as a ratio of one of the inferior-limb blood pressure and the superior-limb blood pressure to the other, and inspects presence or absence of arteriosclerosis based on the thus calculated index.

For example, in the case where arteriosclerosis obliterans is inspected based on an inferior-and-superior-limb blood-pressure index, the index is calculated by dividing an inferior-limb systolic blood pressure by a superior-limb systolic blood pressure and, if the thus calculated index is greater than 0.9, it is judged that arteriostenosis is absent and, if the index is not greater than 0.9, it is judged that arteriostenosis is suspected.

In the above-indicated inferior-and-superior-limb-blood-pressure-index measuring apparatus, generally, an ankle is selected as the inferior limb and a cuff is worn on the ankle. Meanwhile, an ankle has two thick arteries, i.e., an anterior tibial artery and a posterior tibial artery. There are known some cases where one of the two arteries has stenosis but the other artery does not. As explained above, blood pressure lowers on a distal side of a stenotic portion. Since, however, an ankle has two thick arteries, if only one of the two arteries has stenosis and accordingly a blood pressure of the other artery free of stenosis does not lower, the blood pressure of the other artery is measured as a blood pressure of the ankle. Thus, even if one of the two arteries may have stenosis, a measured blood pressure of the ankle may be normal, and an inferior-and-superior-limb blood-pressure index calculated based on the measured ankle blood pressure may be normal. In this case, the inferior-and-superior-limb blood-pressure index cannot be used for finding arteriostenosis.

SUMMARY OF THE INVENTION

It is therefore an object of the present invention to provide an ankle-blood-pressure measuring apparatus which can measure an ankle blood pressure that can be used for calculating an inferior-and-superior-limb blood-pressure index that can be used for accurately inspecting presence or absence of arteriostenosis of an inferior limb of a living person, and an arteriostenosis inspecting apparatus which can accurately inspect presence or absence of arteriostenosis of an inferior limb of a living person.

The above object has been achieved according to a first aspect of the present invention. According to the first aspect, there is provided an ankle-blood-pressure measuring apparatus for measuring a blood pressure of an ankle of a living subject, comprising an inflatable cuff which is adapted to be worn on the ankle of the subject; a cuff-pressure changing device which decreases a pressure in the cuff from a pressure higher than a systolic blood pressure of the ankle; a distal-pulse-wave detecting device which is adapted to be worn on a distal portion of the subject that is located on a distal side of the ankle and detects a distal pulse wave produced from the distal portion; an increasing-point detecting means for detecting at least one increasing point where a magnitude of the distal pulse wave continuously detected by the distal-pulse-wave detecting device when the pressure of the cuff is decreased by the cuff-pressure changing device, significantly increases; and an ankle-blood-pressure determining device which determines a pressure of the cuff when the increasing-point detecting means detects the second increasing point, as a systolic blood pressure of one of a plurality of tibial arteries of the ankle of the subject that has stenosis.

According to this aspect, when the pressure of the cuff worn on the ankle is decreased, the distal-pulse-wave detecting device worn on the distal portion located on the distal side of the ankle continuously detects the distal pulse wave produced from the distal portion, and the increasing-point detecting means detects the increasing point where the magnitude of the distal pulse wave significantly increases. In the case where only one of anterior and posterior tibial arteries has stenosis, a pressure of the cuff when flow of blood resumes in the stenotic tibial artery is lower than a pressure of the cuff when flow of blood resumes in the non-stenotic tibial artery. Therefore, in the distal portion on the distal side of the cuff, amount of flow of blood significantly largely increases twice. Thus, in this case, the increasing-point detecting means detects two increasing points and accordingly the ankle-blood-pressure determining device determines the pressure of the cuff when the increasing-point detecting means detects the second increasing point, as the systolic blood pressure of the stenotic tibial artery.

The above object has been achieved according to a second aspect of the present invention. According to the second aspect, there is provided an arteriostenosis inspecting apparatus, comprising an ankle-blood-pressure measuring apparatus according to the first aspect; a superior-limb-blood-pressure measuring device which measures a systolic blood pressure of a superior limb of the subject; and an inferior-and-superior-limb-blood-pressure-index determining means for determining an inferior-and-superior-limb blood-pressure index of the subject, based on the systolic blood pressure of the ankle measured by the ankle-blood-pressure measuring apparatus and the systolic blood pressure of the superior limb measured by the superior-limb-blood-pressure measuring device.

If an inferior-and-superior-limb blood-pressure index is determined based on the systolic blood pressure of the stenotic tibial artery, measured by the ankle-blood-pressure measuring apparatus, and presence or absence of arteriostenosis is judged based on the thus determined index, the presence or absence of arteriostenosis can be accurately judged by a living person such as a medical person or the subject. According to this aspect, the inferior-and-superior-limb-blood-pressure-index determining means determines the inferior-and-superior-limb blood-pressure index based on the systolic blood pressure of the stenotic tibial artery, measured by the ankle-blood-pressure measuring apparatus. Therefore, if presence or absence of arteriostenosis is judged based on the thus determined index, it is possible to accurately judge the presence or absence of arteriostenosis.

The above object has been achieved according to a third aspect of the present invention. According to the third aspect, there is provided an arteriostenosis inspecting apparatus, comprising an inflatable cuff which is adapted to be worn on an ankle of a living subject; a cuff-pressure changing device which decreases a pressure in the cuff from a pressure higher than a systolic blood pressure of the ankle; a distal-pulse-wave detecting device which is adapted to be worn on a distal portion of the subject that is located on a distal side of the ankle and detects a distal pulse wave produced from the distal portion; an increasing-point detecting means for detecting at least one increasing point where a magnitude of the distal pulse wave continuously detected by the distal-pulse-wave detecting device when the pressure of the cuff is decreased by the cuff-pressure changing device, significantly increases; and an arteriostenosis judging means for judging that the subject has arteriostenosis, based on a fact that the increasing-point detecting means detects the second increasing point.

As explained above, if only one of the two tibial arteries has stenosis, the increasing-point detecting means detects two increasing points. Thus, based on a fact that the increasing-point detecting means detects the second increasing point, it is possible to judge that the subject has arteriostenosis. According to this aspect, when the pressure of the cuff worn on the ankle is decreased, the distal-pulse-wave detecting device worn on the distal portion located on the distal side of the ankle continuously detects the distal pulse wave produced from the distal portion, and the increasing-point detecting means detects the increasing point where the magnitude of the distal pulse wave significantly increases. In addition, the arteriostenosis judging means judges that the subject has arteriostenosis, based on the fact that the increasing-point detecting means detects the second increasing point. Thus, even in the case where one of the two tibial arteries does not have stenosis but the other tibial artery has stenosis, the present apparatus can judge that the subject has arteriostenosis. This improves the accuracy of judgment of presence or absence of arteriostenosis.

The above object has been achieved according to a fourth aspect of the present invention. According to the fourth aspect, there is provided an arteriostenosis inspecting apparatus, comprising an inflatable cuff which is adapted to be worn on an ankle of a living subject; a cuff-pressure changing device which decreases a pressure in the cuff from a pressure higher than a systolic blood pressure of the ankle; a distal-pulse-wave detecting device which is adapted to be worn on a distal portion of the subject that is located on a distal side of the ankle and detects a distal pulse wave produced from the distal portion; and a display device which displays the distal pulse wave continuously detected by the distal-pulse-wave detecting device when the pressure of the cuff is decreased by the cuff-pressure changing device.

According to the third aspect of the present invention, the arteriostenosis judging means automatically judges whether the subject has arteriostenosis. Meanwhile, if the distal pulse wave is displayed, a living person such as a doctor can judge, based on the thus displayed distal pulse wave, whether the subject has arteriostenosis. According to this aspect, when the pressure of the cuff worn on the ankle is decreased, the distal-pulse-wave detecting device worn on the distal portion located on the distal side of the ankle continuously detects the distal pulse wave produced from the distal portion, and the display device displays the thus detected distal pulse wave. If the distal pulse wave displayed by the display device has two increasing points at each of which the magnitude of the distal pulse wave significantly increases, it is possible to judge that one of the two tibial arteries does not have stenosis but the other tibial artery has stenosis.

The above object has been achieved according to a fifth aspect of the present invention. According to the fifth aspect, there is provided an arteriostenosis inspecting apparatus, comprising an inflatable cuff which is adapted to be worn on an ankle of a living subject; a cuff-pressure changing device which changes a pressure in the cuff; an ankle-pulse-wave detecting device which detects an ankle pulse wave produced from the ankle and transmitted to the cuff; a distal-pulse-wave detecting device which is adapted to be worn on a distal portion of the subject that is located on a distal side of the ankle and detects a distal pulse wave produced from the distal portion; an amplitude-difference-value determining means for determining an amplitude difference value indicating a degree of difference between respective amplitudes of respective heartbeat-synchronous pulses of the ankle pulse wave and the distal pulse wave that are detected by the ankle-pulse-wave detecting device and the distal-pulse-wave detecting device, respectively, in a state in which the pressure of the cuff is made lower than a systolic blood pressure of the ankle by the cuff-pressure changing device; and an arteriostenosis judging means for judging that the subject has arteriostenosis, based on a fact that the amplitude difference value determined by the amplitude-difference-value determining means is greater than a reference value.

In the case where a cuff is worn on an ankle and a distal-pulse-wave detecting device is worn on a distal body portion located on a distal side of the ankle, like each of the above-described aspects, it is possible to judge presence or absence of arteriostenosis of an inferior limb, in particular, arteriostenosis of a distal body portion located on a distal side of an ankle which arteriostenosis cannot be inspected by the above-described inferior-and-superior-limb-blood-pressure-index measuring apparatus. According to this aspect, the ankle pulse wave and the distal pulse wave are detected in the state in which the pressure of the cuff is made lower than the systolic blood pressure of the ankle by the cuff-pressure changing device, and the amplitude-difference-value determining means determines the amplitude difference value indicating the degree of difference between the respective amplitudes of the ankle pulse wave and the distal pulse wave. If the subject has arteriostenosis between the ankle where the cuff is worn and the distal portion where the distal-pulse-wave detecting device is worn, the amplitude of the distal pulse wave is attenuated by the stenosis and accordingly is detected as being smaller than the amplitude of the ankle pulse wave that is not influenced by the stenosis, so that the amplitude-difference-value determining means determines a large amplitude difference value. Thus, the arteriostenosis judging means can judge that the subject has arteriostenosis between the ankle where the cuff is worn and the distal portion where the distal-pulse-wave detecting device is worn, based on the fact that the amplitude difference value determined by the amplitude-difference-value determining means is greater than the reference value.

The above object has been achieved according to a sixth aspect of the present invention. According to the sixth aspect, there is provided an arteriostenosis inspecting apparatus, comprising an inflatable cuff which is adapted to be worn on an ankle of a living subject; a cuff-pressure changing device which changes a pressure in the cuff; an ankle-pulse-wave detecting device which detects an ankle pulse wave produced from the ankle and transmitted to the cuff a distal-pulse-wave detecting device which is adapted to be worn on a distal portion of the subject that is located on a distal side of the ankle and detects a distal pulse wave produced from the distal portion; a phase-difference determining means for determining a difference of respective phases of respective heartbeat-synchronous pulses of the ankle pulse wave and the distal pulse wave that are detected by the ankle-pulse-wave detecting device and the distal-pulse-wave detecting device, respectively, in a state in which the pressure of the cuff is made lower than a systolic blood pressure of the ankle by the cuff-pressure changing device; and an arteriostenosis judging means for judging that the subject has arteriostenosis, based on a fact that the phase difference determined by the phase-difference determining means is greater than a reference value.

Based on a phase difference in place of the amplitude difference employed according to the fifth aspect, it is possible to judge presence or absence of arteriostenosis of a distal body portion located on a distal side of an ankle. According to this aspect, the ankle pulse wave and the distal pulse wave are detected in the state in which the pressure of the cuff is made lower than the systolic blood pressure of the ankle by the cuff-pressure changing device, and the phase-difference determining means determines the difference of respective phases of the ankle pulse wave and the distal pulse wave. If the subject has arteriostenosis between the ankle where the cuff is worn and the distal portion where the distal-pulse-wave detecting device is worn, the phase of the distal pulse wave is delayed by the stenosis, so that the phase-difference determining means determines a large phase difference. Thus, the arteriostenosis judging means can judge that the subject has arteriostenosis between the ankle where the cuff is worn and the distal portion where the distal-pulse-wave detecting device is worn, based on the fact that the phase difference determined by the phase-difference determining means is greater than the reference value.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which:

FIG. 14 is a flow chart representing the essential control functions of the electronic control device, shown in FIG. 13;

DETAILED DESCRIPTION OF PREFERRED EMBODIMENTS

Figure 1:
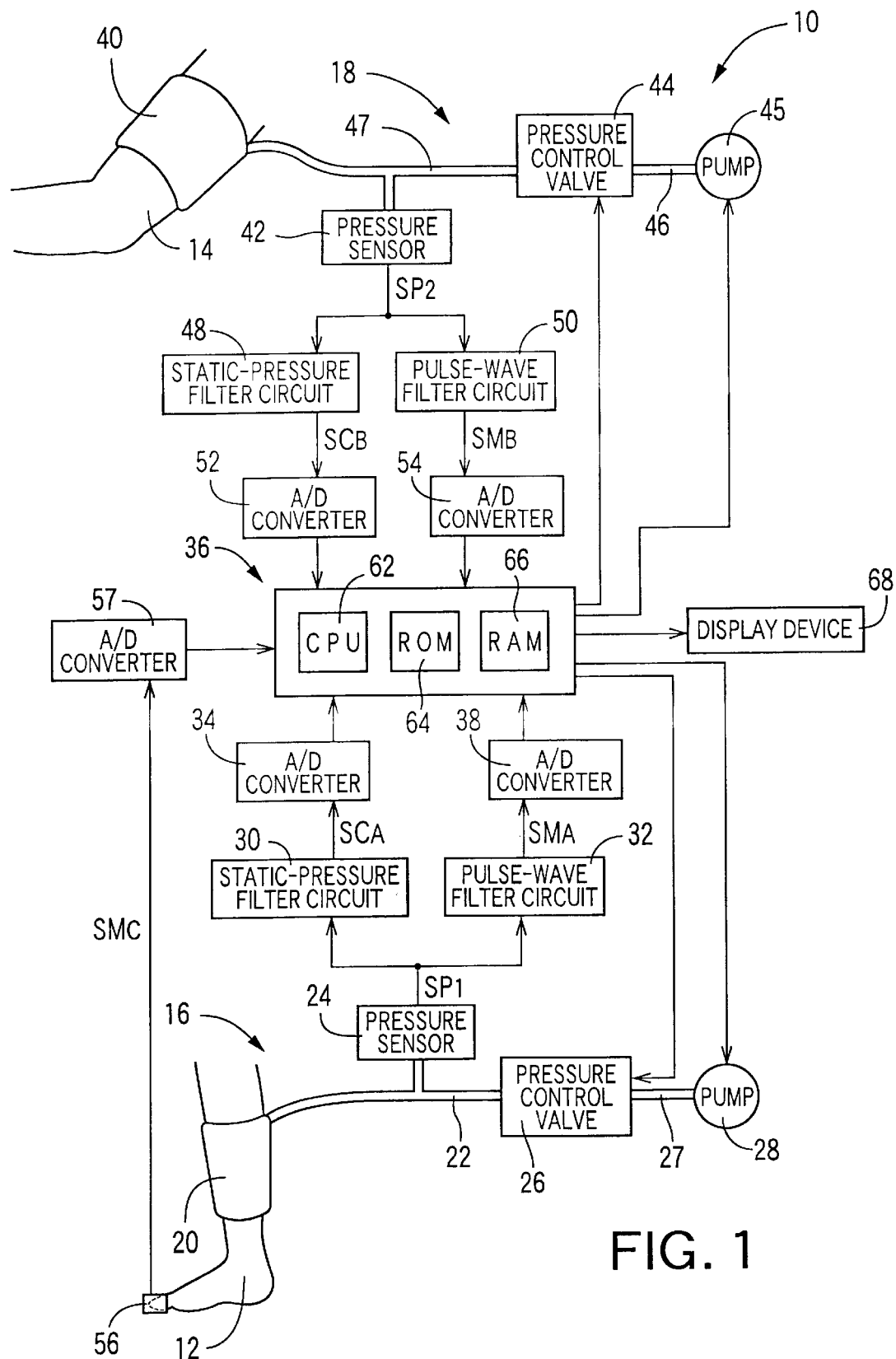
FIG. 1 is a view for explaining a construction of an arteriostenosis inspecting apparatus to which the present invention is applied.

Hereinafter, there will be described a preferred embodiment of the present invention in detail by reference to the drawings. FIG. 1 is a view for explaining a construction of an arteriostenosis inspecting apparatus 10 to which the present invention is applied. The arteriostenosis inspecting apparatus 10 measures an ankle blood pressure BP(A) as a blood pressure BP of an ankle 12 of a patient as a living subject; measures an upper-arm blood pressure BP(B) as a blood pressure BP of an upper arm 14 of the patient; calculates, based on the thus measured ankle blood pressure BP(A) and upper-arm blood pressure BP(B), an ankle-upper-arm blood-pressure index ABI of the patient as an inferior-and-superior-limb blood-pressure index; and inspects, based on the thus calculated ankle-upper-arm blood-pressure index ABI, presence or absence of arteriostenosis of the subject.

In FIG. 1, the arteriostenosis inspecting apparatus 10 includes an ankle-blood-pressure measuring device 16 which measures a blood pressure of the ankle 12, and an upper-arm-blood-pressure measuring device 18 which measures a blood pressure of the upper arm 14 and functions as a superior-limb-blood-pressure measuring device.

The ankle-blood-pressure measuring device 16 includes an ankle cuff 20 which includes a belt-like cloth bag and a rubber bag accommodated in the cloth bag and which is adapted to be wound around the ankle 12 of the patient; a pressure sensor 24 and a pressure control valve 26 which are connected to the ankle cuff 20 via a piping 22; and an air pump 28 which is connected to the pressure control valve 26 via a piping 27. The pressure control valve 26 adjusts a pressure of a pressurized air supplied from the air pump 28, and supplies the pressure-adjusted air to the ankle cuff 20, or discharges the pressurized air from the ankle cuff 22, so as to control an air pressure in the ankle cuff 20.

The pressure sensor 24 detects the air pressure in the ankle cuff 20, and supplies a pressure signal, SP1, representing the detected air pressure, to a static-pressure filter circuit 30 and a pulse-wave filter circuit 32. The static-pressure filter circuit 30 includes a low-pass filter which extracts, from the pressure signal SP1, an ankle-cuff-pressure signal, $SC_A$, representing a static component of the detected air pressure, i.e., a pressing pressure of the ankle cuff 20 (hereinafter, referred to as the ankle cuff pressure, $PC_A$). The filter circuit 30 supplies the ankle-cuff-pressure signal $SC_A$ to an electronic control device 36 via an A/D (analog-to-digital) converter 34.

The pulse-wave filter circuit 32 includes a band-pass filter which extracts, from the pressure signal SP1, an ankle-pulse-wave signal, $SM_A$, representing an ankle pulse wave as an oscillatory component of the detected air pressure that has prescribed frequencies. The filter circuit 32 supplies the ankle-pulse-wave signal $SM_A$ to the control device 36 via an A/D converter 38. Since the ankle pulse wave indicates the oscillation of pressure of the ankle cuff 20, the filter circuit 32 functions as an ankle-pulse-wave detecting device.

The upper-arm-blood-pressure measuring device 18 includes an upper-arm cuff 40, a pressure sensor 42, a pressure control valve 46, and an air pump 45 which have respective constructions identical with those of the counterparts of the ankle-blood-pressure measuring device 16. The upper-arm cuff 40 is wound around the upper arm 14. The pressure control valve 46 is connected to the air pump 45 via a piping 46; and the upper-arm cuff 40 is connected to the pressure sensor 42 and the pressure control valve 44 via a piping 47. The pressure sensor 42 detects an air pressure in the upper-arm cuff 40, and supplies a pressure signal, SP2, representing the detected air pressure, to a static-pressure filter circuit 48 and a pulse-wave filter circuit 50 which have respective constructions identical with those of the counterparts of the ankle-blood-pressure measuring device 16. The static-pressure filter circuit 48 extracts, from the pressure signal SP2, an upper-arm-cuff-pressure signal, $SC_B$, representing a static component of the detected air pressure, i.e., a pressing pressure of the upper-arm cuff 40 (hereinafter, referred to as the upper-arm-cuff pressure, $PC_B$). The filter circuit 48 supplies the upper-arm-cuff-pressure signal $SC_B$ to the control device 36 via an A/D converter 52. The pulse-wave filter circuit 50 extracts, from the pressure signal SP2, an upper-arm-pulse-wave signal, $SM_B$, representing an upper-arm pulse wave as an oscillatory component of the detected air pressure that has prescribed frequencies. The filter circuit 50 supplies the upper-arm-pulse-wave signal $SM_B$ to the control device 36 via an A/D converter 54.

A photoelectric-pulse-wave sensor 56 functioning as a distal-pulse-wave detecting device is worn on a toe of a foot of the patient, detects a volumetric pulse wave as change of volume of blood in capillaries of the toe, and outputs a volumetric-pulse-wave signal $SM_C$ representing the detected volumetric pulse wave, to the electronic control device 36 via an A/D converter 57. Since the volumetric pulse wave represented by the volumetric-pulse-wave signal $SM_C$ is a pulse wave produced from the toe, it will be referred to as a toe pulse wave. In addition, since the photoelectric-pulse-wave sensor 56 is worn on a distal portion of the patient that is located on a distal side of the ankle where the ankle cuff 20 is worn, the toe pulse wave detected by the sensor 56 is a distal pulse wave.

Figure 2:
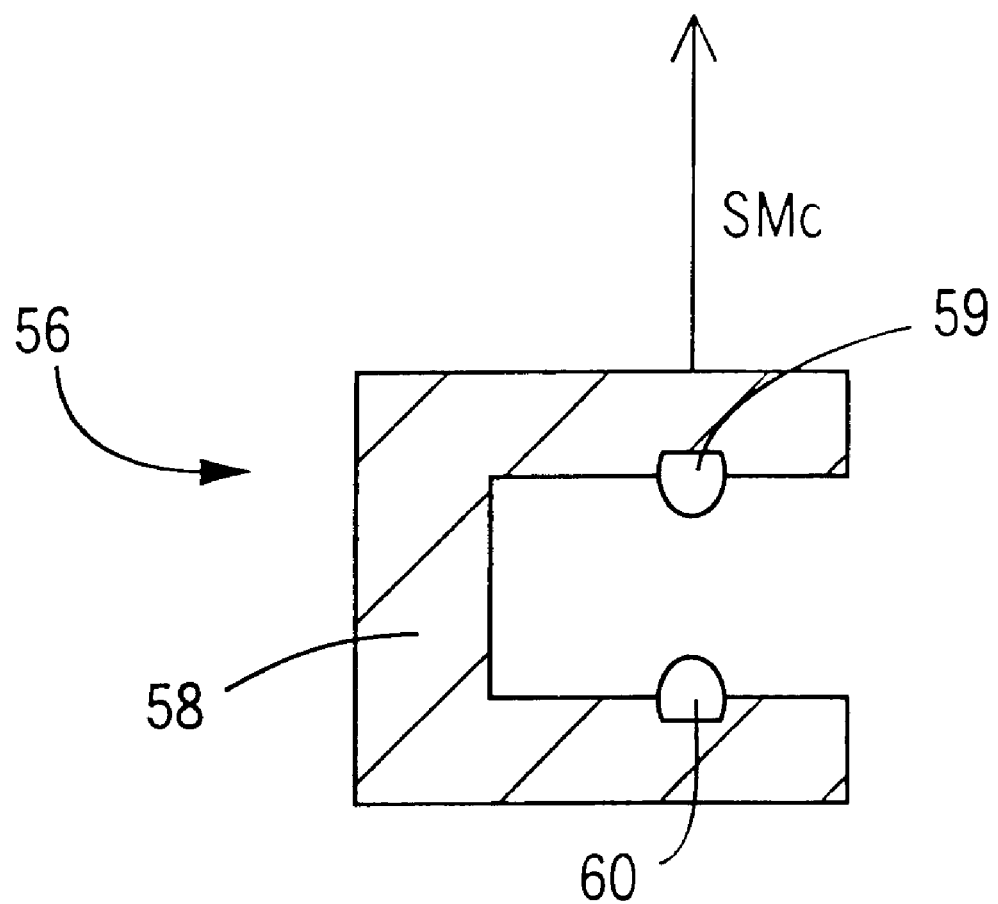
FIG. 2 is a view for explaining a construction of a photoelectric-pulse-wave sensor shown in FIG. 1.

FIG. 2 shows a construction of the photoelectric-pulse-wave sensor 56. The sensor. 56 includes a housing 58 which can accommodate a body portion of the patient such as a toe; a light emitting element 59 which emits, toward the skin of the subject, a red or infrared light having a wavelength that can be reflected by hemoglobin, preferably, a light having a wavelength of about 800 nm that is not influenced by blood oxygen saturation; and a light detecting element 60 which is opposite to the light emitting element 59 and detects the light transmitted through the body portion of the subject.

The control device 36 is essentially provided by a microcomputer including a CPU (central processing unit) 62, a ROM (read only memory) 64, a RAM (random access memory) 66, and an I/O (input-and-output) port, not shown, and the CPU 62 processes signals according to the programs pre-stored in the ROM 64, while utilizing the data-storing function of the RAM 66. The CPU 62 outputs, from the I/O port, drive signals to the air pumps 28, 45 and the pressure control valves 26, 44 so as to control the respective operations thereof and thereby control the respective air pressures of the ankle cuff 20 and the upper-arm cuff 40. In addition, the CPU 62 processes signals supplied to the control device 36, so as to determine an ankle blood pressure BP(A), an upper-arm blood pressure BP(B), and an ankle-and-upper-arm blood-pressure index ABI, and control a display device 68 to display the thus determined pressure and index values.

Figure 3:
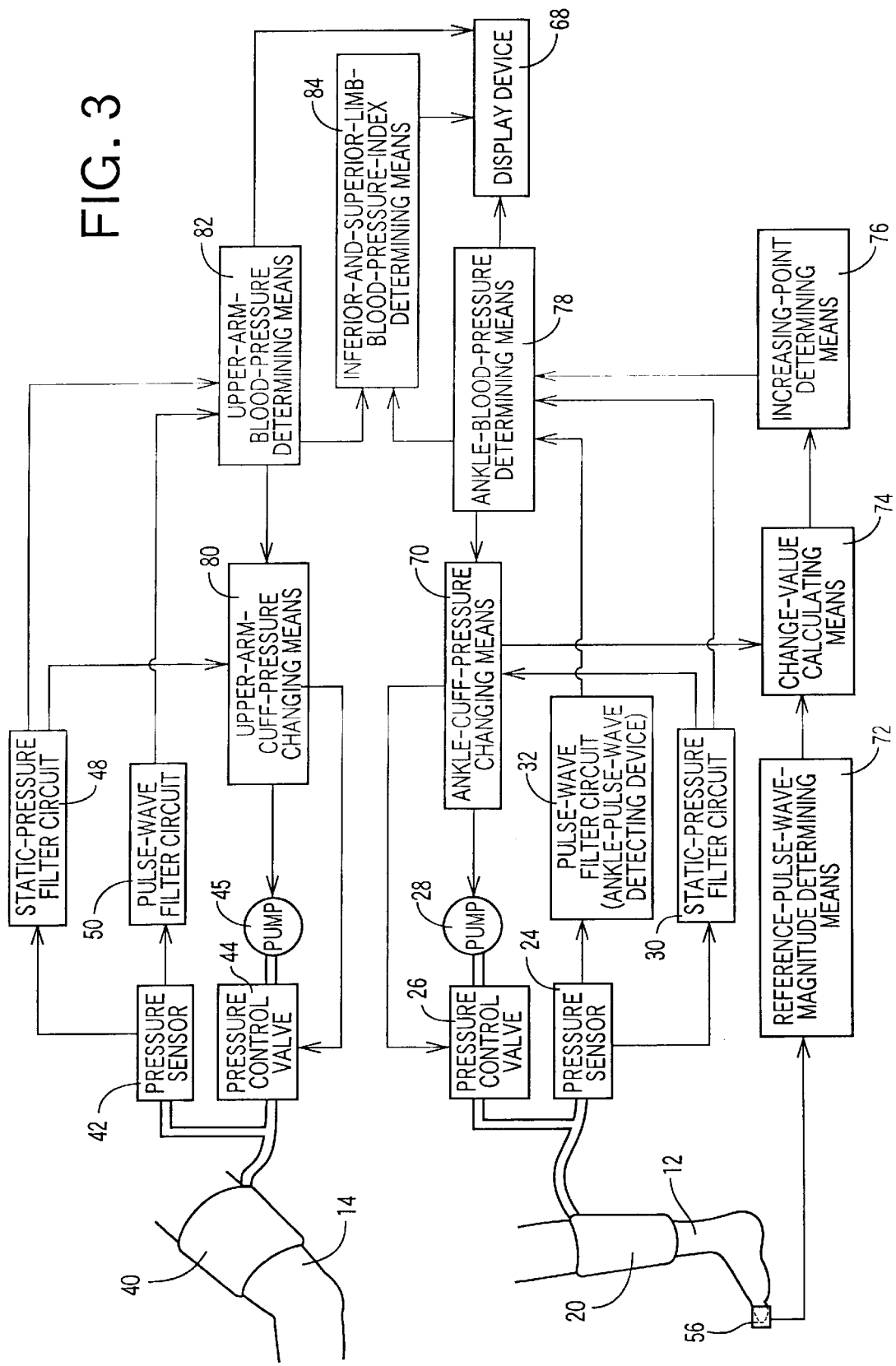
FIG. 3 is a diagrammatic view for explaining essential control functions of an electronic control device of the inspecting apparatus of FIG. 1.

FIG. 3 is a diagrammatic view for explaining essential control functions of the electronic control device 36. An ankle-cuff-pressure changing device or means 70 controls, according to a command signal supplied from an ankle-blood-pressure determining means 78, described later, and based on the ankle-cuff-pressure signal $SC_A$ supplied from the static-pressure filter circuit 30, the air pump 28 and the pressure control valve 26 connected thereto, so as to change the ankle cuff pressure $PC_A$, as follows: First, the changing means 70 quickly increases the ankle cuff pressure $PC_A$ UP to a prescribed first target pressure $PC_{M1}$ (e.g., 240 mmHg) which would be higher than a systolic blood pressure $BP(A)_{SYS}$ of the ankle 12, and subsequently slowly decreases the ankle cuff pressure $PC_A$ at a rate of about 3 mmHg/sec. Finally, after determination of a diastolic blood pressure $BP(A)_{DIA}$ of the ankle, the changing means 70 releases the ankle cuff pressure $PC_A$ to an atmospheric pressure. In the present arteriosclerosis inspecting apparatus 10, an ankle-cuff-pressure changing device is provided by the ankle-cuff-pressure changing means 70; the air pump 28 and the pressure control valve 26 that are controlled by the changing means 70; and the pressure sensor 24 and the static-pressure filter circuit 30 that cooperate with each other to supply the ankle cuff pressure $PC_A$ to the changing means 70.

A reference-pulse-wave-magnitude determining device or means 72 iteratively determines a reference pulse-wave magnitude with respect to a length of the toe pulse wave continuously detected by the photoelectric-pulse-wave sensor 56 while the ankle cuff pressure $PC_A$ is slowly decreased by the ankle-cuff-pressure changing means 70, said length being detected in each time period that is so prescribed as to be equal to from one heartbeat of the subject to several heartbeats of the subject. The reference pulse-wave magnitude may be the average magnitude, the greatest magnitude, or the smallest magnitude of the length of the toe pulse wave detected in each prescribed time period. A change-value calculating device or means 74 calculates a change value (e.g., a rate of change or an amount of change) of each reference pulse-wave magnitude determined by the determining means 72, from its preceding reference pulse-wave magnitude determined by the same 72. Since the thus calculated change value is free from influences caused by the change of magnitude of toe pulse wave corresponding to each heartbeat of the subject, it accurately represents a change of flow amount of blood caused by the decreasing of pressure of the ankle cuff 20.

Figure 4:
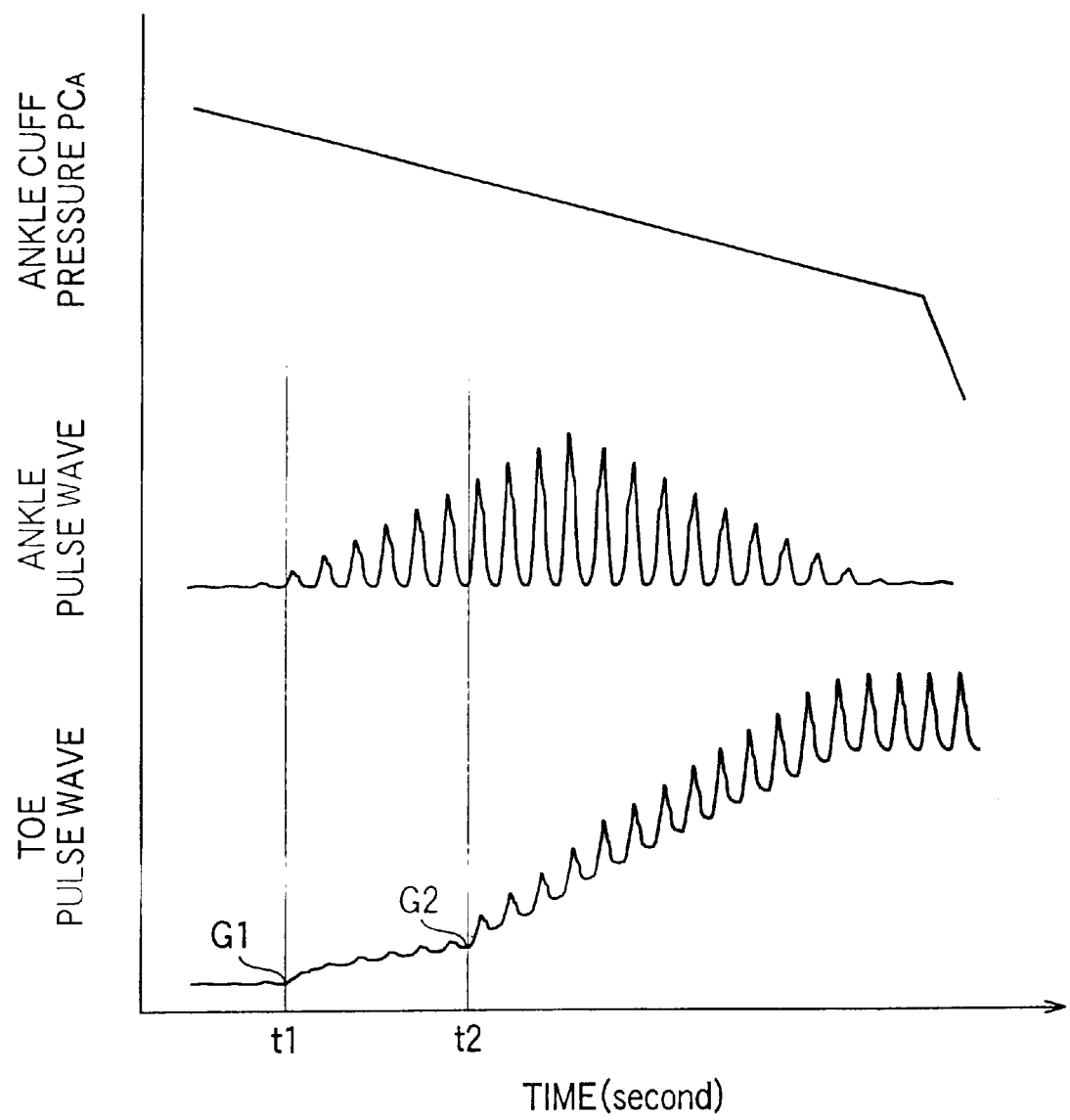
FIG. 4 is a graph showing respective changes of an ankle pulse wave and a toe pulse wave that are detected when an ankle cuff pressure $PC_A$ is decreased by an ankle-cuff-pressure changing means shown in FIG. 3.

An increasing-point detecting device or means 76 calculates a rate of change of each change value determined by the change-value calculating means 74 from its preceding change value determined by the same 74 and detects a point where the thus calculated rate of change is greater than a prescribed reference value TH, as an increasing point, G, where the magnitude of toe pulse wave significantly increases. FIG. 4 illustratively shows respective changes of the ankle pulse wave and the toe pulse wave that are detected when the ankle cuff pressure $PC_A$ is decreased by the ankle-cuff-pressure changing means 70. When the ankle cuff pressure $PC_A$ is made lower than a higher one of respective systolic blood pressure of the anterior and posterior tibial arteries of the ankle 12, flow of blood resumes in the ankle 12, at a time, t1, shown in FIG. 4. If the flow of blood resumes in the ankle 12, flow of blood also resumes in a distal portion located on a distal side of the ankle 12 and accordingly the magnitude of toe pulse wave significantly increases. Thus, the first increasing point G1 is detected at the time t1. In the case where neither the anterior tibial artery nor the posterior tibial artery has stenosis, respective blood pressure of the two arteries do not differ from each other so largely, and accordingly the flow of blood resumes at substantially the same time in the two arteries of the ankle 12. On the other hand, if one of the two arteries of the ankle 12 has stenosis, the blood pressure of the stenotic artery is lowered by the stenosis and accordingly the flow of blood resumes at a delayed time in the stenotic artery. When the ankle cuff pressure $PC_A$ is decreased to a pressure lower than the systolic blood pressure of the stenotic artery, the flow of blood also resumes in the stenotic artery and accordingly the amount of blood flowing in the distal portion located on the distal side of the ankle 12 significantly increases. Therefore, the second increasing point, G2, is detected at a time, t2, shown in FIG. 4.

An ankle-blood-pressure determining device or means 78 determines change of the ankle cuff pressure $PC_A$ and change of respective amplitudes of successive heartbeat-synchronous pulses of the ankle pulse wave, based on the ankle-cuff-pressure signal $SC_A$ and the ankle-pulse-wave signal $SM_A$ that are continuously supplied from the static-pressure filter circuit 30 and the pulse-wave filter circuit 32, respectively, when the ankle cuff pressure $PC_A$ is slowly decreased by the ankle-cuff-pressure changing means 70, and additionally determines, according to a well-known oscillometric algorithm, blood-pressure values of the ankle 12, i.e., an ankle systolic blood pressure $BP(A)_{SYS}$, an ankle mean blood pressure $BP(A)_{MEAN}$, and an ankle diastolic blood pressure $BP(A)_{DIA}$. For example, an ankle systolic blood pressure $BP(A)_{SYS}$ is determined as a value of the ankle cuff pressure $PC_A$ when the amplitude of the ankle pulse wave significantly increases, because the flow of blood in the ankle 12 resumes at that pressure value during the decreasing of the ankle cuff pressure $PC_A$. In addition, when the increasing-point detecting means 76 detects the second increasing point G2, the ankle-blood-pressure determining means 78 determines a value of the ankle cuff pressure $PC_A$ at the time of detection of the second increasing point G2, as a second ankle systolic blood pressure $BP(A)_{SYS2}$.

An upper-arm-cuff-pressure changing device or means 80 controls, according to a command signal supplied from an upper-arm-blood-pressure determining means 82, described later, and based on the upper-arm-cuff-pressure signal $SC_B$ supplied from the static-pressure filter circuit 50, the air pump 45 and the pressure control valve 44 connected thereto, so as to change the upper-arm cuff pressure PCB, as follows: First, the changing means 80 quickly increases the upper-arm cuff pressure $PC_B$ UP to a prescribed second target pressure $PC_{M2}$ (e.g., 180 mmHg) which would be higher than a systolic blood pressure $BP(A)_{SYS}$ of the upper arm 14, and subsequently slowly decreases the upper-arm cuff pressure $PC_B$ at a rate of about 3 mmHg/sec. Finally, after determination of a diastolic blood pressure $BP(B)_{DIA}$ of the upper arm, the changing means 80 releases the upper-arm cuff pressure $PC_B$ to an atmospheric pressure.

An upper-arm-blood-pressure determining device or means 82 determines change of the upper-arm cuff pressure PCB and change of respective amplitudes of successive heartbeat-synchronous pulses of the upper-arm pulse wave, based on the upper-arm-cuff-pressure signal $SC_B$ and the upper-arm-pulse-wave signal $SM_B$ that are continuously supplied from the static-pressure filter circuit 48 and the pulse-wave filter circuit 50, respectively, when the upper-arm cuff pressure $PC_B$ is slowly decreased by the upper-arm-cuff-pressure changing means 80, and additionally determines, according to the well-known oscillometric algorithm, blood-pressure values of the upper arm 14, i.e., an upper-arm systolic blood pressure $BP(B)_{SYS}$, an upper-arm mean blood pressure $BP(B)_{MEAN}$, and an upper-arm diastolic blood pressure $BP(B)_{DIA}$.

An inferior-and-superior-limb-blood-pressure-index determining device or means 84 determines, if the ankle-blood-pressure determining means 78 has determined the second ankle systolic blood pressure $BP(A)_{SYS2}$, an ankle-and-upper-arm blood-pressure index ABI of the subject, based on the second ankle systolic blood pressure $BP(A)_{SYS2}$ and the upper-arm systolic blood pressure $BP(B)_{SYS}$ determined by the upper-arm-blood-pressure determining means 82 and, if not, determines an ankle-and-upper-arm blood-pressure index ABI of the subject, based on the ankle systolic blood pressure $BP(A)_{SYS}$ determined by the ankle-blood-pressure determining means 78 and the upper-arm systolic blood pressure $BP(B)_{SYS}$ determined by the upper-arm-blood-pressure determining means 82. Here, an ankle-and-upper-arm blood-pressure index ABI is obtained by dividing the second ankle systolic blood pressure $BP(A)_{SYS2}$ or the ankle systolic blood pressure $BP(A)_{SYS}$ by the upper-arm systolic blood pressure $BP(B)_{SYS}$, or dividing the upper-arm systolic blood pressure $BP(B)_{SYS}$ by the second ankle systolic blood pressure $BP(A)_{SYS2}$ or the ankle systolic blood pressure $BP(A)_{SYS}$.

Figure 5:
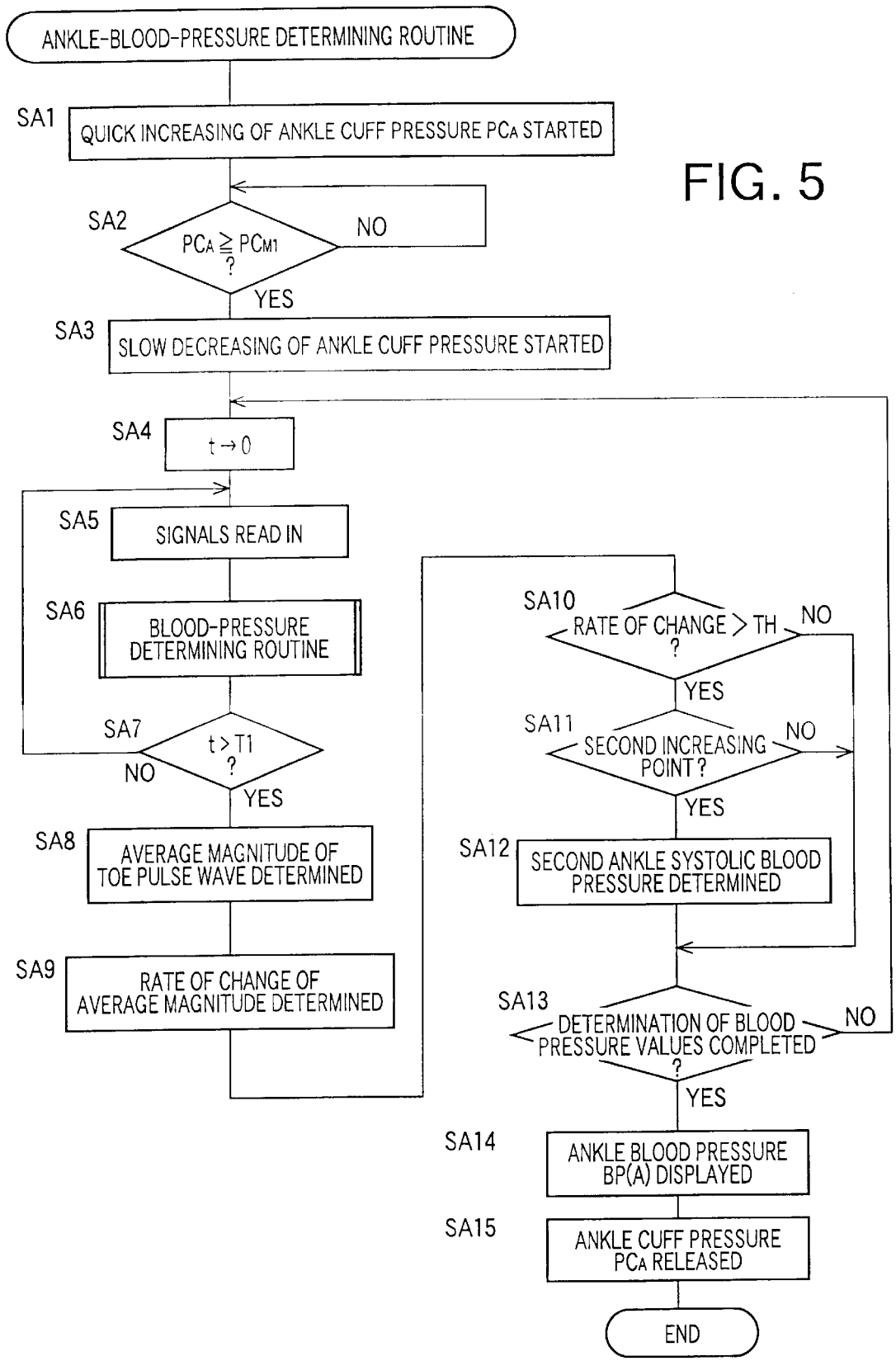
FIG. 5 is a flow chart representing an ankle-blood-pressure determining routine as a portion of the essential control functions of the electronic control device, shown in FIG. 3.
Figure 6:
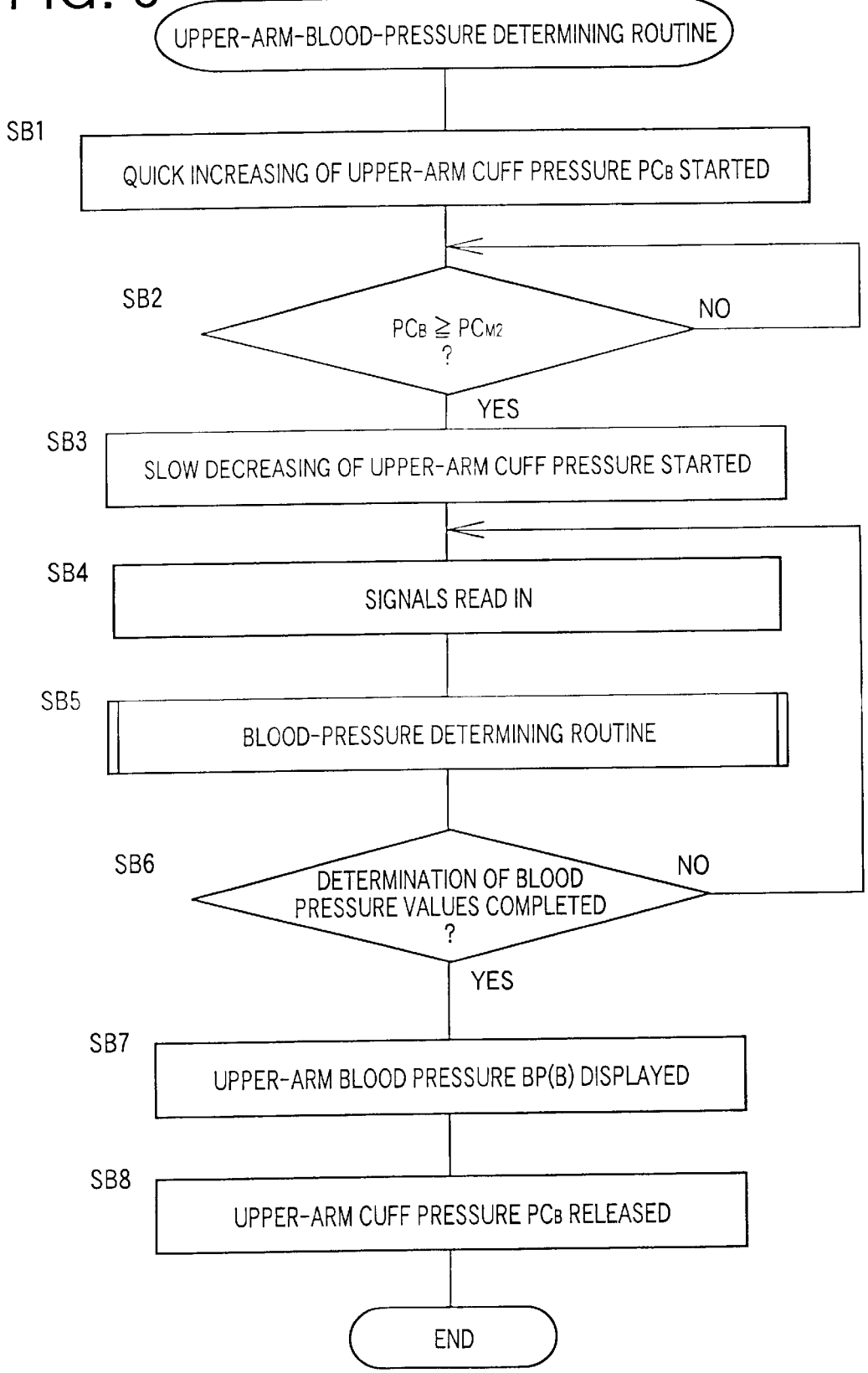
FIG. 6 is a flow chart representing an upper-arm-blood-pressure determining routine as another portion of the essential control functions of the electronic control device, shown in FIG. 3.
Figure 7:
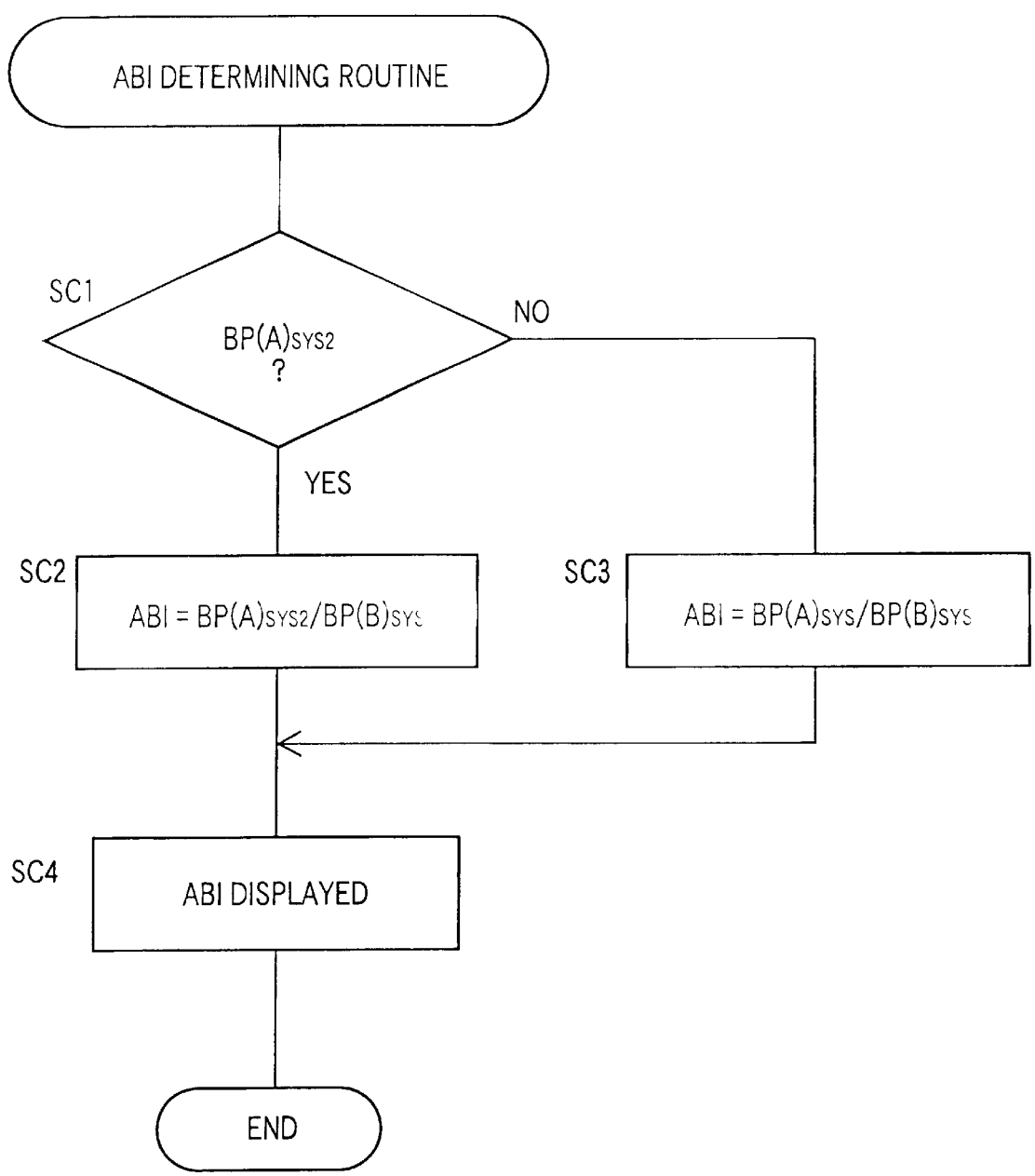
FIG. 7 is a flow chart representing an ankle-upper-arm-blood-pressure-index (ABI) calculating routine as another portion of the essential control functions of the electronic control device, shown in FIG. 3.

FIGS. 5 through 7 show respective charts representing the essential control functions of the electronic control device 36, shown in FIG. 3. FIG. 5 shows an ankle-blood-pressure determining routine; FIG. 6 shows an upper-arm-blood-pressure determining routine; and FIG. 7 shows an ankle-and-upper-arm-blood-pressure-index (ABI) determining routine.

First, the ankle-blood-pressure determining routine of FIG. 5 will be described. The control device carries out Step SA1 (hereinafter, "Step" is omitted) to control the air pump 28 and the pressure control valve 26 so as to start quick increasing of the ankle cuff pressure $PC_A$. Subsequently, at SA2, the control device judges whether the ankle cuff pressure $PC_A$ has been increased up to the first target pressure $PC_{M1}$, e.g., 240 mmHg. Step SA2 is repeated till a positive judgment is made. Meanwhile, if a positive judgment is made at SA2, the control goes to SA3 to stop the air pump 28 and controls the pressure control valve 26 so as to start slow decreasing of the ankle cuff pressure $PC_A$, e.g., at a prescribed rate of 3 mmHg/sec.

Subsequently, at SA4, the control device resets a time measured by a timer, t, to zero (t=0). Then, at SA5, the control device reads in the ankle-cuff-pressure signal $SC_A$ supplied from the static-pressure filter circuit 30, the anklepulse-wave signal $SM_A$ supplied from the pulse-wave filter circuit 32, and the volumetric-pulse-wave signal, $SM_C$, supplied from the photoelectric-pulse-wave sensor 56.

Subsequently, at SA6, the control device carries out a blood-pressure determining routine. More specifically described, the control device determines, based on the ankle-cuff-pressure signal $SC_A$ and the ankle-pulse-wave signal $SM_A$ read in at SA5, respective values of the ankle cuff pressure $PC_A$ and respective amplitudes of successive heartbeat-synchronous pulses of the ankle pulse wave, and determines, based on the thus determined respective values of the ankle cuff pressure $PC_A$ and the thus determined respective amplitudes of successive heartbeat-synchronous pulses of the ankle pulse wave, an ankle systolic blood pressure $BP(A)_{SYS}$, an ankle mean blood pressure $BP(A)_{MEAN}$, and an ankle diastolic blood pressure $BP(A)_{DIA}$ of the subject, according to a well-known oscillometric blood-pressure-determination algorithm.

Then, at SA7, the control device judges whether the time measured by the timer t has exceeded a time period, T1, that is pre-set at a time duration corresponding to one heartbeat of the subject. If a negative judgment is made at SA7, the control goes back to SA5 and the following steps, so as to continue reading in the ankle-cuff-pressure signal $SC_A$, the ankle-pulse-wave signal $SM_A$, and the volumetric-pulse-wave signal $SM_C$, and continue carrying out the blood-pressure determining routine based on the thus read-in signals.

Meanwhile, if a positive judgment is made at SA7, the control goes to SA8 corresponding to the reference-pulse-wave-magnitude determining means 72. At SA8, the control device calculates an average magnitude of the length of the toe pulse wave which length has been read in during the time period T1 while SA5 through SA7 are repeated.

Then, at SA9, the control device divides the current average magnitude calculated at SA8 in the current control cycle according to the ankle-blood-pressure determining routine, by the preceding average magnitude calculated at SA8 in the preceding control cycle according to the same routine, and thereby obtains a rate of change of the current average magnitude. SA9 corresponds to the change-value determining means 74.

Subsequently, at SA10, the control device judges whether the rate of change determined at SA9 is greater than a reference value TH that is experimentally determined in advance. A positive judgment made at SA10 means that the average magnitude of each length of the toe pulse wave, detected during the time period T1, has significantly increased, i.e., that an increasing point G has occurred. Thus, a positive judgment made at SA10 means that an increasing point G has been detected. SA10 corresponding to the increasing-point detecting means 76. Regarding the toe pulse wave shown in FIG. 4, a positive judgment is made at SA10, at the time t1 or at the time t2.

If a negative judgment is made at SA10, the control jumps to SA13. On the other hand, if a positive judgment is made at SA10, the control goes to SA11 to judge whether the increasing point G detected at SA10 is the second increasing point G2. A positive judgment made at SA11 means that the flow of blood resumes in one of the anterior and posterior tibial arteries that has the lower systolic blood pressure. In this case, the control goes to SA12 to determine the current value of the ankle cuff pressure $PC_A$, i.e., the value of the ankle cuff pressure $PC_A$ represented by the ankle-cuff-pressure signal $SC_A$ read in at SA5 in the current control cycle, as a second ankle systolic blood pressure $BP(A)_{SYS2}$.

By the way, the first increasing point G1 is detected at SA10, at the time t1 shown in FIG. 4, and, based on the first increasing point, the ankle systolic blood pressure $BP(A)_{SYS}$ is determined at SA6. Therefore, the second ankle systolic blood pressure $BP(A)_{SYS2}$ is the lower one of the respective systolic blood pressure of the anterior and posterior tibial arteries that is caused by stenosis.

After SA12 is carried out or if a negative judgment is made at SA10 or SA11, the control goes to SA13 to judge whether the determination of ankle blood-pressure values at SA6 has been completed, i.e., whether all the ankle systolic blood pressure $BP(A)_{SYS}$, ankle mean blood pressure $BP(A)_{MEAN}$, and ankle diastolic blood pressure $BP(A)_{DIA}$ have been determined. If a negative judgment is made at SA13, the control goes back to SA4 and the following steps so as to further read in the ankle-cuff-pressure signal $SC_A$, the ankle-pulse-wave signal $SM_A$, and the volumetric-pulse-wave signal $SM_C$, and continue carrying out, based on the thus read-in signals, the determination of the ankle blood-pressure values BP(A) including the second ankle systolic blood pressure $BP(A)_{SYS2}$. In the embodiment shown in FIG. 5, SA6 and SA11 through SA13 correspond to the ankle-blood-pressure determining means 78.

Meanwhile, if a positive judgment is made at SA13, the control goes to SA14 so as to operate the display device 68 to display the ankle systolic blood pressure $BP(A)_{SYS}$, the ankle mean blood pressure $BP(A)_{MEAN}$, and the ankle diastolic blood pressure $BP(A)_{DIA}$. Then, at SA15, the control device controls the pressure control valve 26 to release the ankle cuff pressure $PC_A$ to an atmospheric pressure, thereby finishing the pressing of the ankle 12 with the ankle cuff 20. In the embodiment shown in FIG. 5, SA1 through SA3 and SA15 correspond to the ankle-cuff-pressure changing means 70.

Next, the upper-arm-blood-pressure determining routine of FIG. 6 will be described. The upper-arm-blood-pressure determining routine may be carried out concurrently with the ankle-blood-pressure determining routine of FIG. 5, on an interruption or time-sharing basis, or may be carried out immediately before or after the routine of FIG. 5 is carried out.

First, at SB1, the control device controls the air pump 45 and the pressure control valve 44 so as to start quick increasing of the upper-arm cuff pressure PCB. Subsequently, at SB2, the control device judges whether the upper-arm cuff pressure $PC_B$ has been increased up to the second target pressure $PC_{M2}$, e.g., 180 mmHg. Step SB2 is repeated till a positive judgment is made. Meanwhile, if a positive judgment is made at SB2, the control goes to SB3 to stop the air pump 45 and control the pressure control valve 44 so as to start slow decreasing of the upper-arm cuff pressure PCB, e.g., at a prescribed rate of about 3 mmHg/sec.

Subsequently, at SB4, the control device reads in the upper-arm-cuff-pressure signal $SC_B$ supplied from the static-pressure filter circuit 48, and the upper-arm-pulse-wave signal $SM_B$ supplied from the pulse-wave filter circuit 50. Subsequently, at SB5, the control device carries out the same blood-pressure determining routine as that employed at SA6 of FIG. 5, so as to determine an upper-arm systolic blood pressure $BP(B)_{SYS}$, an upper-arm mean blood pressure $BP(B)_{MEAN}$, and an upper-arm diastolic blood pressure $BP(B)_{DIA}$ of the subject.

Then, at SB6, the control device judges whether the determination of upper-arm blood-pressure values at SB5 has been completed, i.e., whether all the upper-arm systolic blood pressure $BP(B)_{SYS}$, upper-arm mean blood pressure $BP(B)_{MEAN}$, and upper-arm diastolic blood pressure $BP(B)_{DIA}$ have been determined. If a negative judgment is made at SB6, the control goes back to SB4 and the following steps so as to further read in the upper-arm cuff-pressure signal $SC_B$ and the upper-arm-pulse-wave signal $SM_B$, and continue carrying out the blood-pressure determining routine. Thus, SB5 and SB6 correspond to the upper-arm-blood-pressure determining means 82.

Meanwhile, if a positive judgment is made at SB6, the control goes to SB7 so as to operate the display device 68 to display the upper-arm systolic blood pressure $BP(B)_{SYS}$, the upper-arm mean blood pressure $BP(B)_{MEAN}$, and the upper-arm diastolic blood pressure $BP(B)_{DIA}$. Then, at SB8, the control device controls the pressure control valve 44 to release the upper-arm cuff pressure $PC_B$ to an atmospheric pressure, thereby finishing the pressing of the upper arm 14 with the upper-arm cuff 40. In the embodiment shown in FIG. 6, SB1 through SB3 and SB8 correspond to the upper-arm-cuff-pressure changing means 80.

Next, the ankle-and-upper-arm-blood-pressure-index (ABI) determining routine of FIG. 7 will be described. This routine corresponds to the inferior-and-superior-limb-blood-pressure-index determining means 84. First, at SC1, the control device judges whether, in the ankle-blood-pressure determining routine of FIG. 5, the second ankle systolic blood pressure $BP(A)_{SYS2}$ has been determined. If a positive judgment is made at SC1, the control goes to SC2 to calculate an ankle-upper-arm blood-pressure index ABI by dividing the second ankle systolic blood pressure $BP(A)_{SYS2}$ by the upper-arm systolic blood pressure $BP(B)_{SYS}$. On the other hand, if a negative judgment is made at SC1, the control goes to SC3 to calculate an ankle-upper-arm blood-pressure index ABI by dividing the ankle systolic blood pressure $BP(A)_{SYS}$ by the upper-arm systolic blood pressure $BP(B)_{SYS}$. Then, at SC4, the control device operates the display device 68 to display the ankle-upper-arm blood-pressure index ABI calculated at SC2 or SC3.

In the embodiment employing the above-explained flow chart, while the ankle cuff pressure $PC_A$ is slowly, decreased, the photoelectric-pulse-wave sensor 56 worn on the toe corresponding to the ankle 12 on which the ankle cuff 20 is worn continuously detects the toe pulse wave. At SA8 (the reference-pulse-wave-magnitude determining means 72), the control device determines an average magnitude of the toe pulse wave detected during each time period T1; at SA9 (the change-value calculating means 74), the control device calculates a rate of change of each average magnitude; and at SA10 (the increasing-point detecting means 76), the control device detects, based on the thus calculated rate-of-change values, an increasing point G where the magnitude of the toe pulse wave significantly increases. In the case where only one of the two tibial arteries has stenosis, the control device detects, at SA10 (the increasing-point detecting means 76), detects two increasing points G and accordingly the control device determines, at SA12 (the ankle-blood-pressure determining means 78), an ankle cuff pressure $PC_A$ when the control device detects, at SA10 (the increasing-point detecting means 76), detects the second increasing point G2, as a systolic blood pressure of the stenotic tibial artery, i.e., a second systolic blood pressure $BP(A)_{SYS2}$.

In the embodiment employing the above-explained flow chart, the control device calculates, at SC1 through SC4 (the inferior-and-superior-limb blood-pressure index determining means 84), an inferior-and-superior-limb blood-pressure index ABI of the subject based on the systolic blood pressure of the stenotic tibial artery, i.e., the second systolic blood pressure $BP(A)_{SYS2}$, measured by the ankle-blood-pressure measuring device 16. Based on the thus determined index ABI, a medical person can accurately judge whether the subject has arteriostenosis.

Hereinafter, there will be described another embodiment of the present invention. The same reference numerals as used in the preceding, first embodiment are used to designate the corresponding elements of the present, second embodiment, and the description thereof is omitted.

Figure 8:
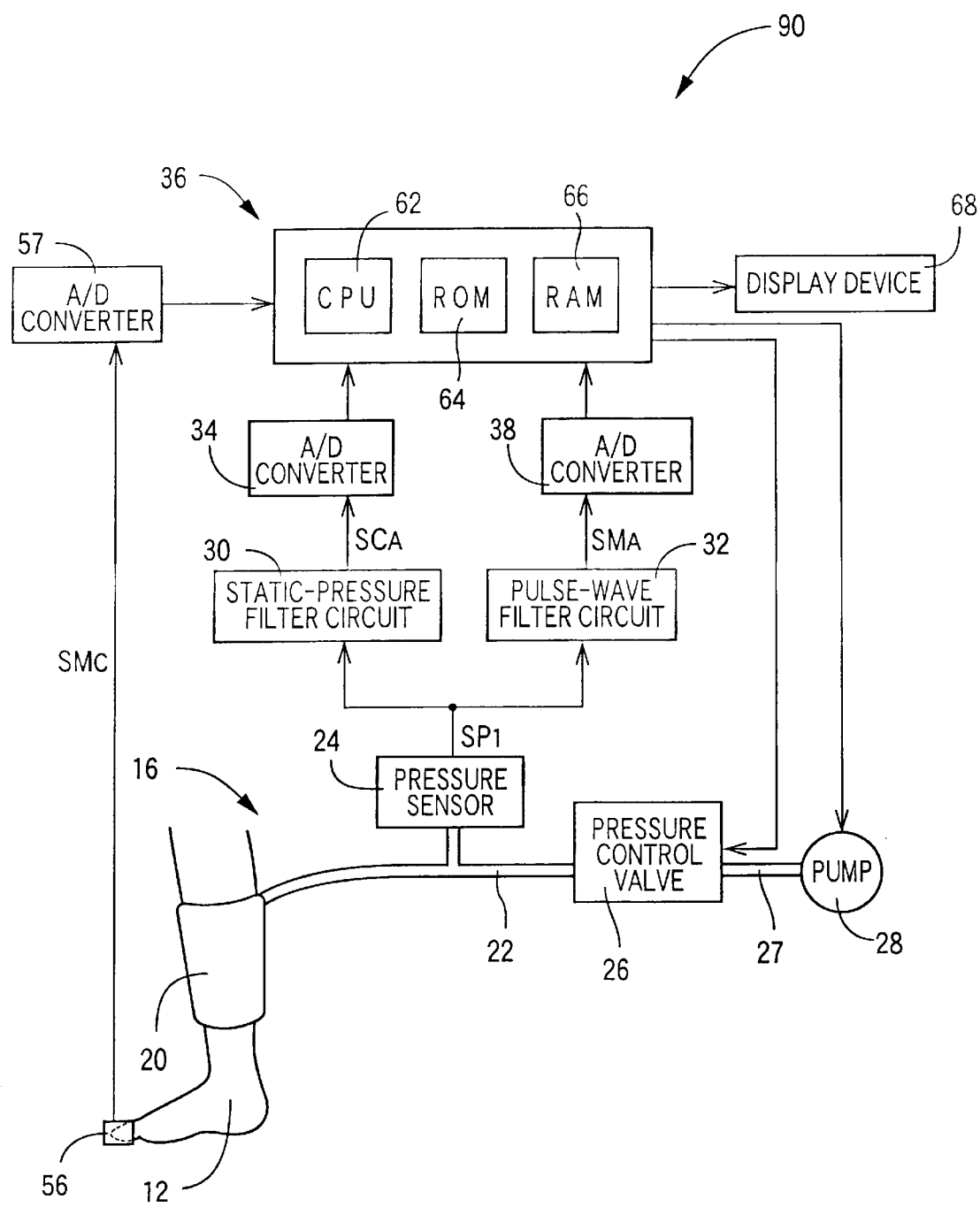
FIG. 8 is a view for explaining a construction of another arteriostenosis inspecting apparatus as a second embodiment of the present invention.

FIG. 8 is a view for explaining a construction of another arteriostenosis inspecting apparatus 90 as the second embodiment. The arteriostenosis inspecting apparatus 90 shown in FIG. 8 differs from the apparatus 10 shown in FIG. 1, in that the apparatus 90 does not employ the upper-arm-blood-pressure measuring device 18.

Figure 9:
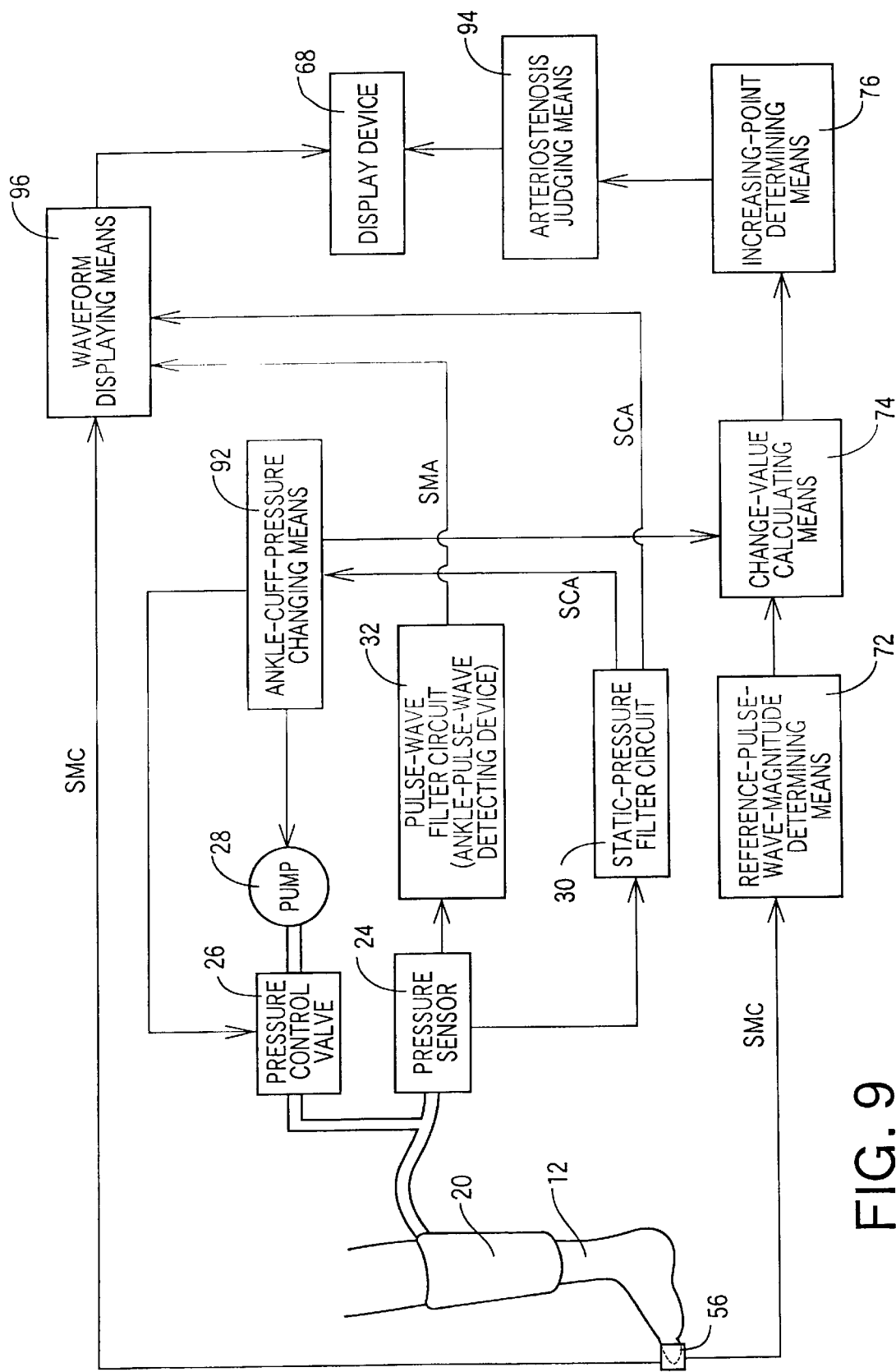
FIG. 9 is a diagrammatic view for explaining essential control functions of an electronic control device of the inspecting apparatus of FIG. 8.

FIG. 9 is a diagrammatic view for explaining essential control functions of an electronic control device 36 of the arteriostenosis inspecting apparatus 90. An ankle-cuff-pressure changing device or means 92 controls, based on the ankle-cuff pressure signal $SC_A$ supplied from the static-pressure filter circuit 30, the air pump 28 and the pressure control valve 26 connected thereto, so as to quickly increase the ankle cuff pressure $PC_A$ UP to the prescribed first target pressure $PC_{M1}$ (e.g., 240 mmHg) which would be higher than the systolic blood pressure $BP(A)_{SYS}$ of the ankle 12, and subsequently slowly decrease the ankle cuff pressure $PC_A$ at the rate of about 3 mmHg/sec. Finally, after the ankle cuff pressure $PC_A$ has been decreased down to a prescribed third target pressure $PC_{M3}$, the changing means 92 releases the ankle cuff pressure $PC_A$ down to an atmospheric pressure. The third target pressure $PC_{M3}$ is so prescribed as to be lower than the ankle systolic blood pressure $BP(A)_{SYS}$ even if the systolic blood pressure $BP(A)_{SYS}$ may be lowered by the presence of arteriostenosis.

A reference-pulse-wave-magnitude determining device or means 72, a change-value calculating device or means 74, and an increasing-point detecting device or means 76 of the arteriostenosis inspecting apparatus 90 are identical with the counterparts 72, 74, 76 of the apparatus 10. Therefore, the increasing-point detecting means 76 detects an increasing point G where the magnitude of the toe pulse wave continuously detected by the photoelectric-pulse-wave sensor 56 significantly increases.

An arteriostenosis judging device or means 94 judges that the subject has arteriostenosis based on a fact that the increasing-point detecting means 76 has detected the second increasing point G2, and operates the display device 68 to display characters or symbols indicating that the subject has arteriostenosis.

A waveform displaying device or means 96 operates the display device 68 to display, with a time-wise change of the ankle cuff pressure $PC_A$, respective waveforms of the ankle pulse wave and the toe pulse wave that are continuously detected by the pulse-wave filter circuit 32 and the photoelectric-pulse-wave sensor 56, respectively, when the ankle cuff pressure $PC_A$ is slowly decreased by the ankle-cuff-pressure changing means 92. FIG. 4 shows the ankle cuff pressure $PC_A$, the ankle pulse wave, and the toe pulse wave that are displayed by the waveform displaying means 96.

Figure 10:
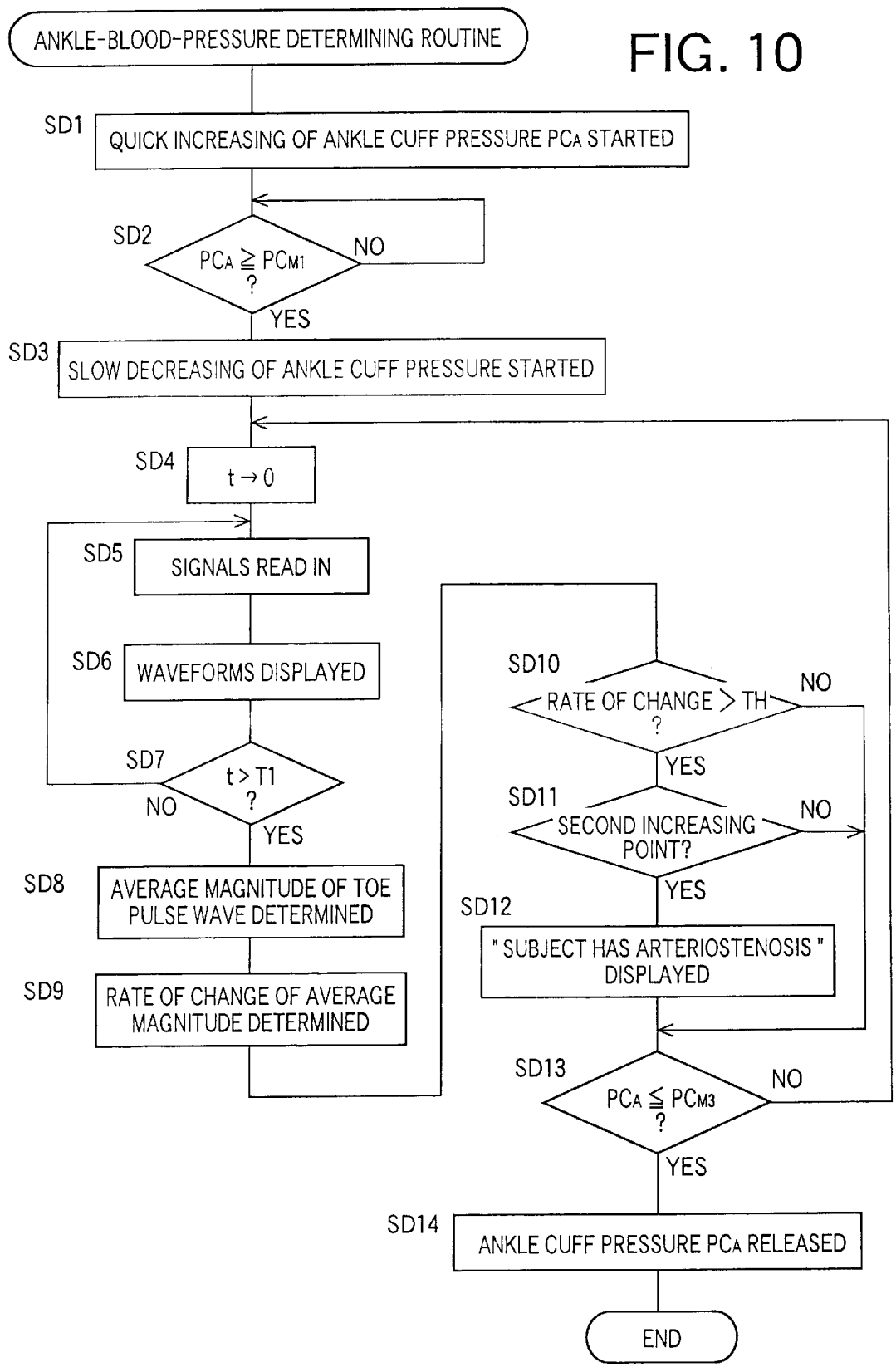
FIG. 10 is a flow chart representing the essential control functions of the electronic control device, shown in FIG. 9.

FIG. 10 shows a flow chart representing the essential control functions of the electronic control device 36, shown in FIG. 9. SD1 through SD5 shown in FIG. 10 are identical with SA1 through SA5 shown in FIG. 5. At SD6 corresponding to the waveform displaying means 96, the control device operates the display device 68 to display the ankle cuff pressure $PC_A$, the ankle pulse wave, and the toe pulse wave, based on the ankle-cuff-pressure signal $SC_A$, the ankle-pulse-wave signal $SM_A$, and the volumetric-pulse-wave signal $SM_C$, each read in at SD5, respectively.

SD7 through SD11 are identical with SA7 through SA11 shown in FIG. 5. Thus, at SD11, the control device judges whether the rate-of-change values iteratively calculated at SD9 have exceeded the reference value TH for the second time. A positive judgment made at SD11 means that the anterior tibial artery or the posterior tibial artery has stenosis. Therefore, the control goes to SD12 to operate the display device 68 to display an indication, "SUBJECT HAS ARTERIOSTENOSIS". Thus, SD11 and SD12 correspond to the arteriostenosis judging means 94.

If a negative judgment is made at SD10 or SD11, or after SD12 is carried out, then the control goes to SD13 to judge whether the ankle cuff pressure $PC_A$ has been decreased down to a third target pressure $PC_{M3}$, e.g., 90 mmHg. If a negative judgment is made at SD13, the control goes back to SD4 and the following steps, so that while the ankle cuff pressure $PC_A$ is slowly decreased, the control device continues displaying the pulse waves and detecting the increasing points G. On the other hand, if a positive judgment is made at SD13, the control goes to SD14 to operate the pressure control valve 26 to release the ankle cuff pressure $PC_A$ down to an atmospheric pressure, thereby ending the pressing of the ankle 12 with the ankle cuff 20. In the embodiment shown in FIG. 10, SD1 through SD3, SD13 and SD14 correspond to the ankle-cuff-pressure changing means 92.

In the present embodiment, while the ankle cuff pressure $PC_A$ is slowly decreased, the photoelectric-pulse-wave sensor 56 worn on the toe corresponding to the ankle 12 on which the ankle cuff 20 is worn continuously detects the toe pulse wave. At SD8 (the reference-pulse-wave-magnitude determining means 72), the control device determines an average magnitude of the toe pulse wave detected during each time period T1; at SD9 (the change-value calculating means 74), the control device calculates a rate of change of each average magnitude; and at SD10 (the increasing-point detecting means 76), the control device detects, based on the thus calculated rate-of-change values, an increasing point G where the magnitude of the toe pulse wave significantly increases. In the case where only one of the two tibial arteries has stenosis, the control device detects, at SD10 (the increasing-point detecting means 76), detects two increasing points G. Therefore, at SD11 (the arteriostenosis judging means 94), the control device judges that the subject has arteriostenosis, based on a fact that the control device has detected, at SD 10 (the increasing-point detecting means 76), detects the second increasing point G2.

Also, in the present embodiment, while the ankle cuff pressure $PC_A$ is slowly decreased, the photoelectric-pulse-wave sensor 56 worn on the toe corresponding to the ankle 12 on which the ankle cuff 20 is worn continuously detects the toe pulse wave. The thus detected toe pulse wave is displayed by the display device 68. If the toe pulse wave displayed by the display device 68 has two increasing points G at each of which the magnitude of the pulse wave significantly increases, a medical person can judge that even if one of the two tibial arteries may not have stenosis, the other tibial artery has stenosis.

Figure 11:
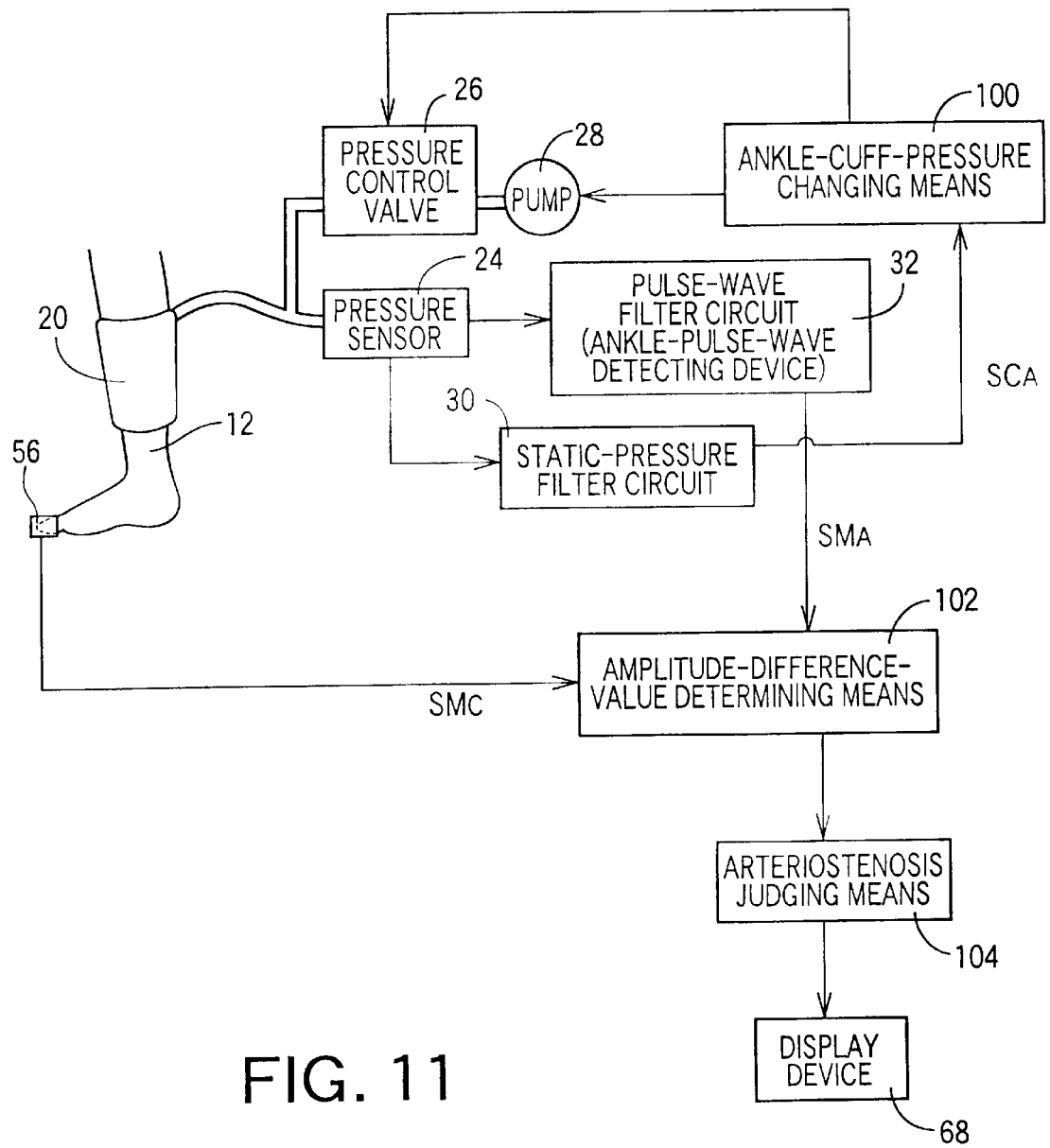
FIG. 11 is a diagrammatic view for explaining essential control functions of an electronic control device of another arteriostenosis inspecting apparatus as a third embodiment of the present invention.

Next, there will be described yet another embodiment of the present invention that also relates to an arteriostenosis inspecting apparatus. This arteriostenosis inspecting apparatus as the third embodiment differs from the apparatus 90 as the second embodiment, only with respect to some control functions of an electronic control device 36. FIG. 11 is a diagrammatic view for explaining essential control functions of the electronic control device 36 of the arteriostenosis inspecting apparatus as the third embodiment.

An ankle-cuff-pressure changing device or means 100 changes and keeps the ankle cuff pressure $PC_A$ to and at a pulse-wave detection pressure. The pulse-wave detection pressure is so prescribed as to be lower than a diastolic blood pressure of the ankle where the ankle cuff 20 is worn, and assure that an ankle-pulse-wave signal $SM_A$ extracted by the pulse-wave filter circuit 32 has a sufficiently great magnitude. For example, the pulse-wave detection pressure is prescribed at 50 mmHg. In the present embodiment, an ankle-cuff-pressure changing device is provided by the ankle-cuff-pressure changing means 100; the air pump 28 and the pressure control valve 26 that are controlled by the changing means 100; and the pressure sensor 24 and the static-pressure filter circuit 30 that cooperate with each other to supply the ankle-cuff-pressure signal $SC_A$ to the changing means 100.

An amplitude-difference-value determining device or means 102 first determines respective amplitudes of respective heartbeat-synchronous pulses of the ankle pulse wave and the toe pulse wave respectively represented by the ankle-pulse-wave signal $SM_A$ and the volumetric-pulse-wave signal $SM_C$ that are supplied from the pulse-wave filter circuit 32 and the photoelectric-pulse-wave sensor 56, respectively, in the state in which the ankle cuff pressure $PC_A$ is kept at the pulse-wave detection pressure by the ankle-cuff-pressure changing means 100. Then, the amplitude-difference determining means 102 determines an amplitude difference value indicating a degree of difference between the thus determined two amplitudes. The amplitude difference value may be a value obtained by subtracting one of the two amplitudes from the other amplitude, or a value obtained by dividing one of the two amplitudes by the other amplitude.

Even if there may be no arteriostenosis between the ankle 12 and the toe, the amplitude of the toe pulse wave detected from the toe is smaller than that of the ankle pulse wave detected from the ankle. If there is arteriostenosis between the ankle 12 and the toe, the amplitude of the toe pulse wave is much smaller than that of the ankle pulse wave. Therefore, the amplitude difference value is increased by the presence of arteriostenosis. Therefore, if the amplitude difference value determined by the amplitude-difference-value determining means 102 is greater than a prescribed reference value, an arteriostenosis judging device or means 104 judges that the subject has arteriostenosis between the ankle where the cuff is worn and the toe where the photoelectric-pulse-wave sensor 56 is worn, and operates the display device 68 to display this judgment.

Figure 12:
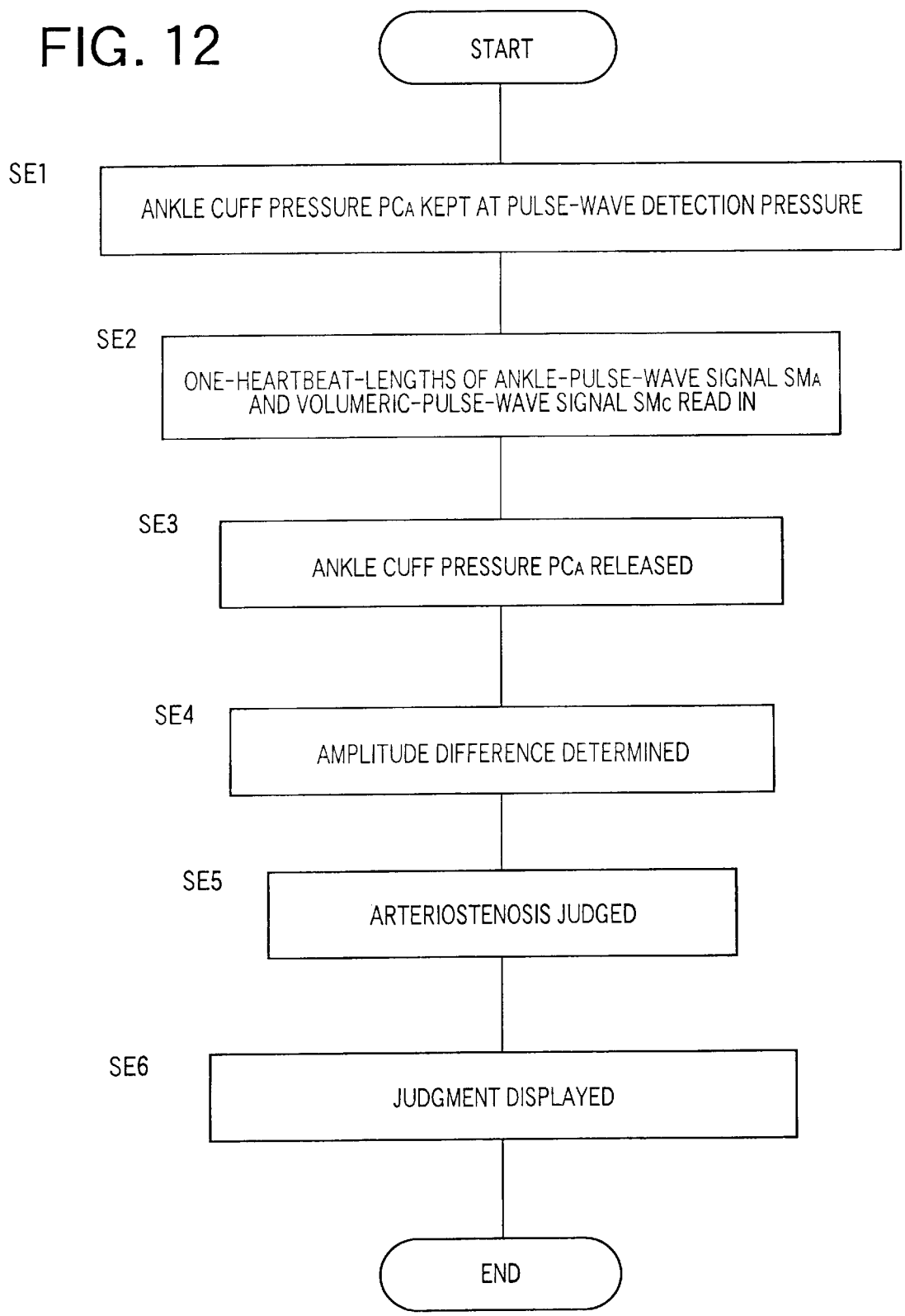
FIG. 12 is a flow chart representing the essential control functions of the electronic control device, shown in FIG. 11.

FIG. 12 shows a flow chart representing the essential control functions of the electronic control device 36, shown in FIG. 11. First, at SE1, the control device operates the air pump 28 and the pressure control valve 26 so as to change the ankle cuff pressure $PC_A$ to a pulse-wave detection pressure, e.g., 50 mmHg, and then stops the air pump 28 and closes the pressure control valve 26 so as to keep the ankle cuff pressure $PC_A$ at the pulse-wave detection pressure.

Then, at SE2, the control device reads in respective one-heartbeat lengths of the ankle-pulse-wave signal $SM_A$ and the volumetric-pulse-wave signal $SM_C$ in the state in which the ankle cuff pressure $PC_A$ is kept at the pulse-wave detection pressure. Subsequently, at SE3, the control device operates the pressure control valve 26 to release the ankle cuff pressure $PC_A$ to an atmospheric pressure.

Then, the control goes to SE4 corresponding to the amplitude-difference-value determining means 102. At SE4, the control device determines, based on the respective one-heartbeat lengths of the ankle-pulse-wave signal $SM_A$ and the volumetric-pulse-wave signal $SM_C$ read in at SE2, respective amplitudes of respective heartbeat-synchronous pulses of the ankle pulse wave and the toe pulse wave, and additionally determines an amplitude difference by subtracting the amplitude of the toe pulse wave from that of the ankle pulse wave.

Subsequently, the control goes to SE5 and SE6 corresponding to the arteriostenosis judging means 104. First, at SE5, the control device judges whether the amplitude difference determined at SE4 is greater than a prescribed reference value. If yes, the control device judges that the subject has arteriostenosis; and if no, the control device judges that the subject does not have arteriostenosis. Then, at SE6, the control device operates the display device 68 to display the judgment made at SE5.

In the present embodiment, in the state in which the ankle cuff pressure $PC_A$ is kept at the pulse-wave detection pressure at SE1 (the cuff-pressure changing means 100), the ankle pulse wave and the distal pulse wave are detected at SE2, and the amplitude difference between the respective amplitudes of the ankle pulse wave and the distal pulse wave is determined at SE4 (the amplitude-difference-value determining means 102). If the amplitude difference determined at SE4 (the amplitude-difference-value determining means 102) is greater than the prescribed reference value, the control device judges, at SE5 (the arteriostenosis judging means 104), whether the subject has arteriostenosis between the ankle where the ankle cuff 20 is worn and the toe where the photoelectric-pulse-wave sensor 56 is worn.

Figure 13:
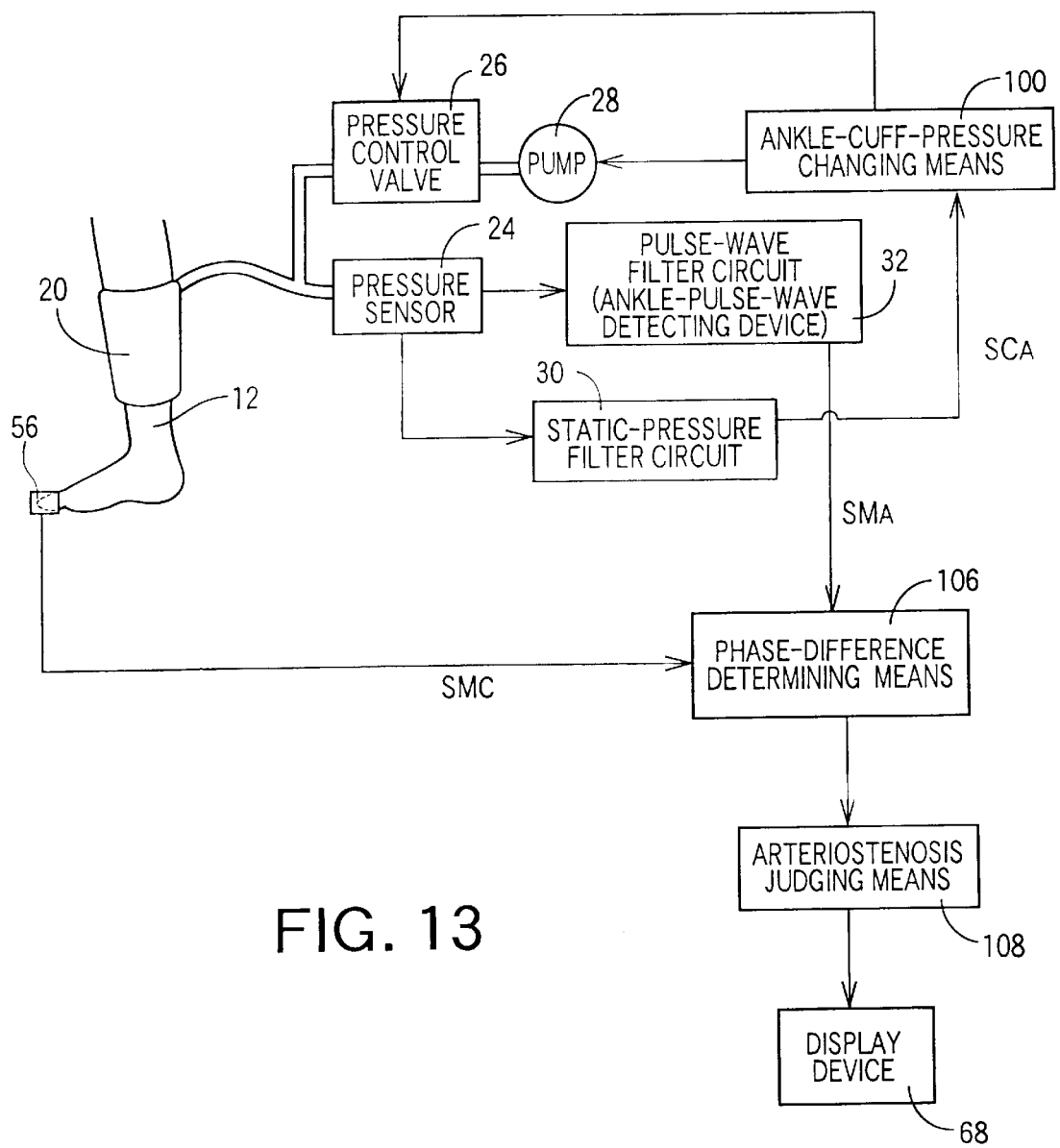
FIG. 13 is a diagrammatic view for explaining essential control functions of an electronic control device of another arteriostenosis inspecting apparatus as a fourth embodiment of the present invention.

Next, there will be described a fourth embodiment of the present invention that also relates to an arteriostenosis inspecting apparatus. This arteriostenosis inspecting apparatus as the fourth embodiment differs from the arteriostenosis inspecting apparatus as the third embodiment, only with respect to some control functions of an electronic control device 36. FIG. 13 is a diagrammatic view for explaining essential control functions of the electronic control device 36 of the arteriostenosis inspecting apparatus as the fourth embodiment.

The diagrammatic view shown in FIG. 13 differs from that shown in FIG. 11 only in that in FIG. 13 a phase-difference determining device or means 106 is provided in place of the amplitude-difference-value determining means 102 provided in FIG. 11 and in that an arteriostenosis judging device or means 108 provided in FIG. 13 makes a judgment based on a phase difference determined by the phase-difference determining means 106. Hereinafter, only those differences will be explained.

The phase-difference determining means 106 determines a difference between respective phases of respective heartbeat-synchronous pulses of the ankle pulse wave and the toe pulse wave respectively represented by the ankle-pulse-wave signal $SM_A$ and the volumetric-pulse-wave signal $SM_C$ that are supplied from the pulse-wave filter circuit 32 and the photoelectric-pulse-wave sensor 56, respectively, in the state in which the ankle cuff pressure $PC_A$ is kept at the pulse-wave detection pressure by the ankle-cuff-pressure changing means 100. If there is arteriostenosis between the ankle 12 and the toe, the phase of the toe pulse wave detected from the toe is delayed from that of the ankle pulse wave detected from the ankle. Therefore, the phase difference is increased by the presence of arteriostenosis. Therefore, if the phase difference determined by the phase-difference determining means 106 is greater than a prescribed reference value, an arteriostenosis judging device or means 108 judges that the subject has arteriostenosis between the ankle where the cuff is worn and the toe where the photoelectric-pulse-wave sensor 56; is worn, and operates the display device 68 to display this judgment.

FIG. 14 shows a flow chart representing the essential control functions of the electronic control device 36, shown in FIG. 13. SF1 through SF3 shown in FIG. 14 are identical with SE1 through SE3 shown in FIG. 12. Thus, in the state in which the ankle cuff pressure $PC_A$ is kept at the pulse-wave detection pressure, the control device reads in respective one-heartbeat lengths of the ankle-pulse-wave signal $SM_A$ and the volumetric-pulse-wave signal $SM_C$ and, subsequently at SE3, the control device operates the pressure control valve 26 to release the ankle cuff pressure $PC_A$ to an atmospheric pressure.

Then, the control goes to SF4 corresponding to the phase-difference determining means 106. At SF4, the control device determines, based on the respective one-heartbeat lengths of the ankle-pulse-wave signal $SM_A$ and the volumetric-pulse-wave signal $SM_C$ read in at SE2, respective phases of respective heartbeat-synchronous pulses of the ankle pulse wave and the toe pulse wave, and additionally determines a phase difference by subtracting the phase of the toe pulse wave from that of the ankle pulse wave.

Subsequently, the control goes to SF5 and SF6 corresponding to the arteriostenosis judging means 108. First, at SF5, the control device judges whether the phase difference determined at SF4 is greater than a prescribed reference value. If yes, the control device judges that the subject has arteriostenosis; and if no, the control device judges that the subject does not have arteriostenosis. Then, at SF6, the control device operates the display device 68 to display the judgment made at SF5.

In the present embodiment, in the state in which the ankle cuff pressure $PC_A$ is kept at the pulse-wave detection pressure at SF1 (the cuff-pressure changing means 100), the ankle pulse wave and the distal pulse wave are detected at SF2, and the phase difference between the respective phases of the ankle pulse wave and the distal pulse wave is determined at SF4 (the phase-difference determining means 106). If the phase difference determined at SF4 (the phase-difference determining means 106) is greater than the prescribed reference value, the control device judges, at SF5 (the arteriostenosis judging means 108), whether the subject has arteriostenosis between the ankle where the ankle cuff 20 is worn and the toe where the photoelectric-pulse-wave sensor 56 is worn.

While the present invention has been described in its embodiment by reference to the drawings, it is to be understood that the invention may otherwise be embodied.

For example, in each of the illustrated embodiments, the photoelectric-pulse-wave sensor 56 is worn on a toe of foot. However, the sensor 56 may be worn on any distal portion located on a distal side of the ankle cuff 20, for example, a proximal portion located on a proximal side of a toe, such as an instep (i.e., a portion above a dorsal pedal artery).

Also, in each of the third and fourth embodiments, the ankle pulse wave and the toe pulse wave are detected in the state in which the ankle cuff pressure $PC_A$ is kept at the pulse-wave detection pressure. However, the ankle pulse wave and the toe pulse wave may be detected in a state in which the ankle cuff pressure $PC_A$ is slowly decreased.

It is to be understood that the present invention may be embodied with other changes, improvements and modifications that may occur to a person skilled in the art without departing from the spirit and scope of the invention defined in the appended claims.

What is claimed is:

1. An ankle-blood-pressure measuring apparatus for measuring a blood pressure of an ankle of a living subject, comprising:

an inflatable cuff which is adapted to be worn on the ankle of the subject;

a cuff-pressure changing device which decreases a pressure in the cuff from a pressure higher than a systolic blood pressure of the ankle;

a distal-pulse-wave detecting device which is adapted to be worn on a distal portion of the subject that is located on a distal side of the ankle and detects a distal pulse wave produced from the distal portion;

an increasing-point detecting means for detecting at least one first increasing point where a magnitude of the distal pulse wave continuously detected by the distal-pulse-wave detecting device when the pressure of the cuff is decreased by the cuff-pressure changing device, significantly increases; and an ankle-blood-pressure determining device which determines a pressure of the cuff when the increasing-point detecting means detects a second increasing point, as a systolic blood pressure of one of a plurality of tibial arteries of the ankle of the subject that has stenosis.

2. An arteriostenosis inspecting apparatus, comprising:

an ankle-blood-pressure measuring apparatus according to claim 1;

a superior-limb-blood-pressure measuring device which measures a systolic blood pressure of a superior limb of the living subject; and an inferior-and-superior-limb-blood-pressure-index determining means for determining an inferior-and-superior-limb blood-pressure index of the subject, based on the systolic blood pressure of the ankle measured by the ankle-blood-pressure measuring apparatus and the systolic blood pressure of the superior limb measured by the superior-limb-blood-pressure measuring device.

3. An ankle-blood-pressure measuring apparatus for measuring a blood pressure of an ankle of a living subject, comprising:

an inflatable cuff which is adapted to be worn on the ankle of the subject;

a cuff-pressure changing device which decreases a pressure in the cuff from a pressure higher than a systolic blood pressure of the ankle;

a distal-pulse-wave detecting device which is adapted to be worn on a distal portion of the subject that is located on a distal side of the ankle and detects a distal pulse wave produced from the distal portion;

an increasing-point detecting device which detects at least one first increasing point where a magnitude of the distal pulse wave continuously detected by the distal-pulse-wave detecting device when the pressure of the cuff is decreased by the cuff-pressure changing device, significantly increases; and an ankle-blood-pressure determining device which determines a pressure of the cuff when the increasing-point detecting device detects a second increasing point, as a systolic blood pressure of one of a plurality of tibial arteries of the ankle of the subject that has stenosis.

4. An arteriostenosis inspecting apparatus, comprising:

an ankle-blood-pressure measuring apparatus according to claim 3;

a superior-limb-blood-pressure measuring device which measures a systolic blood pressure of a superior limb of the living subject; and an inferior-and-superior-limb-blood-pressure-index determining device which determines an inferior-and-superior-limb blood-pressure index of the subject, based on the systolic blood pressure of the ankle measured by the ankle-blood-pressure measuring device and the systolic blood pressure of the superior limb measured by the superior-limb-blood-pressure measuring device.

* * * * *